US008740843B2

(12) United States Patent
Eaton et al.

(10) Patent No.: US 8,740,843 B2
(45) Date of Patent: Jun. 3, 2014

(54) COATED BALLOON CATHETER

(75) Inventors: Elizabeth A. Eaton, Bloomington, IN (US); Gary B. Shirley, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 109 days.

(21) Appl. No.: 13/264,278

(22) PCT Filed: Apr. 8, 2010

(86) PCT No.: PCT/US2010/030355
§ 371 (c)(1),
(2), (4) Date: Nov. 3, 2011

(87) PCT Pub. No.: WO2010/120620
PCT Pub. Date: Oct. 21, 2010

(65) Prior Publication Data
US 2012/0143054 A1 Jun. 7, 2012

Related U.S. Application Data

(60) Provisional application No. 61/168,752, filed on Apr. 13, 2009.

(51) Int. Cl.
*A61M 25/10* (2013.01)
(52) U.S. Cl.
USPC .................. 604/101.02; 604/500; 604/103.01; 604/103.02
(58) Field of Classification Search
USPC .................. 604/96.01, 97.01, 101.02–101.03, 604/101.05, 102.01–102.03, 604/103.01–103.02, 912, 915, 917, 919, 604/528, 500; 606/108, 191–194
See application file for complete search history.

(56) References Cited

U.S. PATENT DOCUMENTS

| 4,921,483 A | 5/1990 | Wijay et al. |
| 5,049,132 A * | 9/1991 | Shaffer et al. ............ 604/101.02 |

(Continued)

FOREIGN PATENT DOCUMENTS

| EP | 1 230 944 A2 | 1/2002 |
| WO | WO 2009/033026 A1 | 3/2009 |

(Continued)

OTHER PUBLICATIONS

Search Report for related PCT Application No. PCT/US2010/030355 mailed Aug. 26, 2010.

*Primary Examiner* — Quynh-Nhu H Vu
(74) *Attorney, Agent, or Firm* — Brinks Gilson & Lione

(57) ABSTRACT

Catheter balloons (10) for delivering a bioactive (260) to a body vessel in a greater amount and/or more quickly are provided, as well as related methods of treatment. The catheter balloon may include a dual balloon assembly at the distal portion (300) of the catheter having an inner balloon (44), an outer balloon (42) with apertures (43) concentrically arrayed around the inner balloon, and a catheter shaft (30) adapted to deliver a carrier (270) through the apertures of the outer balloon. The bioactive is disposed on a portion of at least one of the inner and outer balloon surfaces. Radial outward expansion of the inner balloon urges the outer balloon into contact with the wall of the body vessel. The carrier is introducible within the catheter shaft to pass through the annular lumen (242) between the balloons and through the apertures of the outer balloon. The carrier interacts with the bioactive in order to release a therapeutically effective amount of drug to the wall of the body vessel.

20 Claims, 7 Drawing Sheets

(56) References Cited

U.S. PATENT DOCUMENTS

| | | | |
|---|---|---|---|
| 5,304,121 A * | 4/1994 | Sahatjian | 604/509 |
| 5,746,717 A * | 5/1998 | Aigner | 604/102.03 |
| 5,879,282 A * | 3/1999 | Fischell et al. | 600/3 |
| 6,369,039 B1 * | 4/2002 | Palasis et al. | 514/44 R |
| 6,413,203 B1 * | 7/2002 | Sahatjian | 600/3 |
| 6,544,221 B1 * | 4/2003 | Kokish et al. | 604/103.01 |
| 6,596,818 B1 | 7/2003 | Zamore | |
| 6,939,320 B2 * | 9/2005 | Lennox | 604/103.02 |
| 7,048,714 B2 * | 5/2006 | Richter | 604/103.02 |
| 7,094,765 B1 | 8/2006 | Iversen et al. | |
| 8,182,446 B2 * | 5/2012 | Schaeffer et al. | 604/101.05 |
| 2002/0115559 A1 | 8/2002 | Batchelor et al. | |
| 2004/0073297 A1 | 4/2004 | Rohde et al. | |
| 2004/0224868 A1 | 11/2004 | Meyerhoff et al. | |
| 2004/0243225 A1 * | 12/2004 | Ragheb et al. | 623/1.42 |
| 2005/0250672 A9 | 11/2005 | Speck et al. | |
| 2006/0020243 A1 | 1/2006 | Speck et al. | |
| 2006/0020331 A1 | 1/2006 | Bates et al. | |
| 2006/0032507 A1 * | 2/2006 | Tu | 128/898 |
| 2006/0224115 A1 | 10/2006 | Willard | |
| 2006/0269587 A1 | 11/2006 | Iversen et al. | |
| 2007/0212387 A1 * | 9/2007 | Patravale et al. | 424/422 |
| 2007/0232905 A1 * | 10/2007 | Francis | 600/432 |
| 2008/0075970 A1 | 3/2008 | Suzuki et al. | |
| 2008/0140002 A1 * | 6/2008 | Ramzipoor et al. | 604/103.02 |
| 2008/0195079 A1 | 8/2008 | Moore et al. | |
| 2008/0243103 A1 | 10/2008 | Whetham et al. | |
| 2008/0255510 A1 * | 10/2008 | Wang | 604/103.02 |
| 2008/0300610 A1 | 12/2008 | Chambers | |
| 2009/0136560 A1 * | 5/2009 | Bates et al. | 424/423 |
| 2009/0227948 A1 * | 9/2009 | Chen et al. | 604/103.02 |
| 2009/0254064 A1 * | 10/2009 | Boatman | 604/509 |
| 2010/0069900 A1 | 3/2010 | Shirley et al. | |
| 2010/0268191 A1 * | 10/2010 | Trudel et al. | 604/509 |
| 2010/0305680 A1 * | 12/2010 | Schaaf | 623/1.11 |

FOREIGN PATENT DOCUMENTS

| | | |
|---|---|---|
| WO | WO 2009/036135 A1 | 3/2009 |
| WO | WO 2010/120620 A1 | 10/2010 |
| WO | WO2011/094379 A1 | 8/2011 |

* cited by examiner

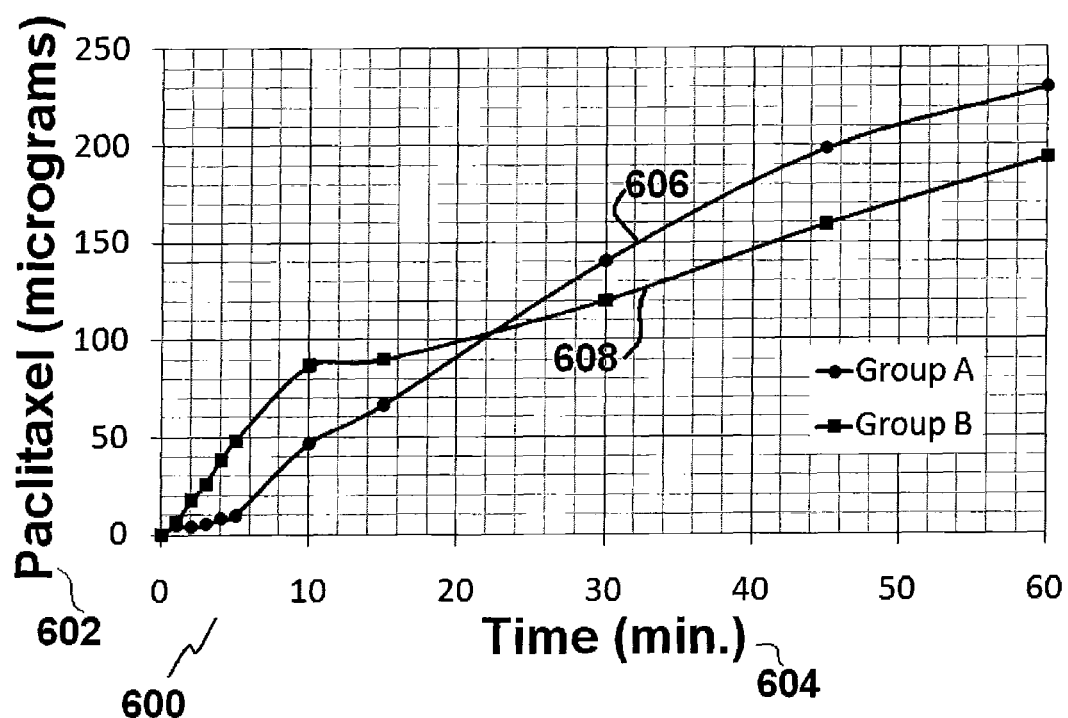

COATED BALLOON CATHETER

This application is a National Stage of International Application PCT/US2010/30355 filed Apr. 8, 2010, which claims the benefit of the filing date under 35U.S.C. §119(e) of Provisional U.S. Patent Application Ser. No. 61/168,752, filed Apr. 13, 2009. The entirety of both applications is hereby incorporated by reference.

TECHNICAL FIELD

The present application relates to medical catheters and more specifically to coated medical catheters useful in delivering a fluid within a body vessel for therapeutic treatment.

BACKGROUND

Although many medical conditions are satisfactorily treated by the general systemic administration of a therapeutic agent, the treatment of many conditions require delivery of the therapeutic agent locally within a body vessel and/or to a selected portion of internal body tissue, without systemic delivery of the therapeutic agent and/or minimizing delivery of the therapeutic agent to surrounding tissue. A systemically administered therapeutic agent may be absorbed not only by the tissues at the target site, but also by other areas of the body. As such, one drawback associated with the systemic administration of therapeutic agents is that areas of the body not needing treatment can also be affected.

Medical delivery catheters provide a minimally invasive means for delivering therapeutic agents to internal body tissue. To provide site-specific localized treatment, balloon catheters may be used to deliver a therapeutic agent directly to the target site within a body vessel. One example of a condition that is beneficially treated by local administration of a therapeutic agent with a balloon catheter is the delivery of a therapeutic agent in combination with percutaneous transluminal coronary angioplasty (PTCA), a technique used to dilate stenotic portions of blood vessels. In such cases, a catheter balloon coated with the therapeutic agent is positioned at a blocked lumen or target site during PTCA, and the balloon is inflated causing dilation of the lumen. The catheter balloon is pressed against the vessel wall for ideally rapid release and absorption of the therapeutic agent by the vessel wall. The balloon is deflated and the catheter is then removed from the target site and the patient's lumen thereby allowing blood to more freely flow through the now less restricted lumen.

Although PTCA and related procedures aid in alleviating intraluminal constrictions, such constrictions or blockages may reoccur in many cases. The cause of these recurring obstructions, termed restenosis, may be due to the body responding to the surgical procedure. Restenosis of the artery may develop over several months after the procedure, and may require another angioplasty procedure or a surgical bypass operation to correct. Proliferation and migration of smooth muscle cells (SMC) from the media layer of the lumen to the intimal layer cause an excessive production of extra cellular matrices (ECM), which is believed to be one of the leading contributors to the development of restenosis. The extensive thickening of tissues narrows the lumen of the blood vessel, constricting or blocking the blood flow through the vessel. Therapeutic agents selected to limit or prevent restenosis may be locally delivered during PTCA from a catheter and/or by placement of a stent configured to continue to release the therapeutic agent after the PTCA procedure. Catheter balloons may be used in combination with stents, synthetic vascular grafts or drug therapies, during the PTCA procedure to reduce or eliminate the incidence of restenosis.

In addition, balloon catheters can be coated with a coating solution including more than just the therapeutic agent. Various configurations of the solution including the therapeutic agent can be applied to the outer surface of the catheter balloon. In preparation of the drug coating solution, several ingredients, such as a therapeutic agent, a contrast agent, an additive, a solvent, and/or others, are mixed and then applied to the catheter balloon. However, this can be problematic. Often, the physical characteristics of these coatings, such as solubility, integrity, and uniformity of the coating, are undesirable. For instance, a result of the added ingredients to the therapeutic agent can unacceptably increase the solubility of the therapeutic agent to the point where, during translation of the balloon catheter to the target site, a substantial portion of the drug coating can wash away in the vessel downstream, leaving a less effective amount for treatment after reaching the target site. Also, the more contrast media mixed with the therapeutic agent results in less crystalline therapeutic agent (i.e., less durable), which can cause the formation of clumps in the coating that can easily flake off during handling or delivering of the balloon catheter. Consequently, there is a high variability in its effectiveness, i.e., inconsistent therapeutic effects, due to these deficiencies, which adversely affects the uniformity and consistency of the drug delivery to the target site.

Other balloon catheter devices have been developed to administer a therapeutic agent locally to tissue while dilating a body vessel, such as during delivery of a therapeutic agent to a dilated portion of a coronary artery during a PTCA procedure. For instance, a therapeutic agent may be administered directly to the target site through small holes or apertures in the wall of a catheter balloon. Other examples include dual balloon catheters for the application of a therapeutic agent to a blood vessel wall. The distal portion of the dual balloon catheter includes an inner balloon enclosed by a porous outer balloon. In operation, a therapeutic agent may be administered through a lumen in communication with the annular space between the inner and the outer balloon in the catheter, and released through an array of minute holes or micropores in the outer balloon as the therapeutic agent flows into the space between the balloons through a lumen in the catheter shaft. The therapeutic agent is released by the action of pressurization in the lumen in communication with the outer balloon and forced out of the holes or micropores. With these dual balloon catheters, the clinician typically has to choose the therapeutic agent and pre-mix the therapeutic agent with a contrast media (e.g., 50/50 mix) at the bedside of the patient, and then introduce the mixture to the dual balloon catheter for administration to the target site.

Thus, what is needed is a drug coated balloon catheter that facilitates delivery of a therapeutic agent to a body vessel wall more uniformly and consistently. Further, what is needed is a drug coated balloon catheter that rapidly delivers more consistently a therapeutically effective amount of drug to a body vessel wall. It would also be desirable to provide the clinician a dual balloon catheter for delivering a therapeutic agent, without the additional steps of measuring and mixing the therapeutic agent at the bedside of a patient.

SUMMARY

Accordingly, drug coated weeping balloon catheters, as well as methods of use thereof, adapted to deliver a bioactive from a surface of a balloon to a body vessel are provided. The weeping balloon catheter can enhance the release of a bioactive into the adjacent or surrounding tissue at a greater amount and/or a quicker rate in order to expedite the medical procedure. Better elution rates of the bioactive may be obtained by providing a carrier to interact with the drug coating of the balloon catheter. A bioactive can be coated on a portion of a surface of a perforated outer balloon or a surface of an inner balloon. The perforated outer balloon allows for the "weeping" or release of a carrier through the apertures of the perforated outer balloon by the urging of an inner balloon that is inflated.

The balloon catheter includes a catheter shaft extending along a longitudinal axis from a proximal end to a distal end. The catheter shaft includes at least one of an inflation lumen, a fluid delivery lumen, and a guide wire lumen. A thermoformable polymer can be disposed within the catheter shaft and about the tubular members. A stiffening member can also be disposed within the catheter shaft adjacent with respect to the tubular members. A portion of the stiffening member can be surrounded by the thermoformable polymer, where the stiffening member is in non-translatable contact with, or fixed within, the thermoformable polymer. The balloon catheter further includes an inner balloon mounted on a distal region of the catheter shaft and in communication with the inflation lumen. The inner balloon is movable between a deflated configuration and an inflated configuration. An outer balloon with a plurality of apertures is disposed about at least a portion of the inner balloon. The outer balloon is movable between a compressed configuration and an expanded configuration. The inner balloon and the outer balloon are configured and oriented such that an annular lumen is defined when the inner balloon is in the inflated configuration and the outer balloon is in the expanded configuration. The annular lumen is in communication with the fluid delivery lumen and the plurality of apertures.

A first composition including a bioactive is included on at least a portion of a surface of one of the balloons: the exterior surface of the outer balloon; the exterior surface of the inner balloon; and/or the interior surface of the outer balloon. A primer layer and/or a barrier layer may also be associated with the first composition and surface of the balloon. The bioactive can be an anti-restenosis agent, an antisense agent, an anti-thrombogenic agent, an antiproliferative agent, and antimitotic agent. The bioactive can further include paclitaxel, rapamycin, a rapamycin derivative, an antisense oligonucleotide, and mTOR inhibitor. A second composition including a carrier configured to enhance the elution rate of the bioactive is adapted to be introduced into the fluid delivery lumen and to be released through the apertures of the outer balloon. The carrier may include another carrier agent adapted to change the effectiveness of the carrier when mixed therewith. Before, during, and/or after release, the carrier interacts with the bioactive for enhanced delivery to the body vessel wall. The carrier can include an imageable component, or even be a diagnostic contrast medium, such as iobitridol, iohexyl, iomeprol, iopamidol, iopentol, iopromide, ioverosl, ioxilan, iotrolan, iodixanol, ioxaglate, and their derivatives.

In a preferred embodiment, the first composition includes a solvent, such as ethanol that can be mixed with bioactive. In this instance, an effective amount of bioactive may be eluted and released to the body vessel within an optimal time allotment of up to about 10 minutes. During the optimal time, the elution rate can be in a range of approximately about 4.5 to about 9.6 micrograms/min up to the first 10 minutes. As a result, less bioactive is required because of the enhancing features of the weeping carrier, which reduces manufacturing costs. It can further reduce the amount of time during which the drug coated weeping balloon must be inflated and used to appose the bioactive to the body vessel wall for transferring a therapeutically effective amount of bioactive and/or further increase the uptake and delivery of the bioactive to the body vessel wall. In one example, between a period of about 2 to 10 minutes, paclitaxel eluted about 200% to about 500% more, and about 2-3 times faster. After delivery, less paclitaxel (about 15% or less) was found on the balloon.

Also provided is a method of delivering a bioactive to a point of treatment with in body vessel is also provided. The method can include one or more of the following steps. A balloon catheter, as described herein, is positioned at the treatment site within the body vessel. The inner balloon is inflated to the inflated configuration to place the outer balloon in contact with the body vessel wall. The exterior surface of the outer balloon, which contacts the body vessel wall, the interior surface of the outer balloon, and/or the exterior surface of the inner balloon can include the first composition that includes the bioactive. The second composition including a carrier is introduced through the fluid delivery lumen and the annular lumen to move the outer balloon to the expanded configuration at a pressure effective to deliver the second composition to the body vessel wall through the apertures of the outer balloon. Preferably, the bioactive includes paclitaxel and the carrier includes a diagnostic contrast medium. With the carrier also being a diagnostic contrast medium, this simplifies the procedures even more since the diagnostic contrast medium can be used for not only diagnostic reasons, but also for further enhancing the elution rate of the bioactive. Thus, since diagnostic contrast medium is typically readily available, only a marginal amount more of diagnostic contrast medium may be needed to complete the elution of the bioactive. The outer balloon remains in contact the body vessel wall for a time sufficient to deliver a therapeutically effective amount of bioactive to the body vessel wall. It is more effective when the contact between the outer balloon and the body vessel wall is maintained for a period of time of up to 22 minutes, or even for the first ten minutes when the elution rate can be about 9.6 micrograms/min. The amount of bioactive released and/or elution rate can be controlled by mixing a first carrier, e.g., a contrast medium, with a second carrier, e.g., saline. In this instance, the balloon catheter comes from the manufacturing facility with a pre-determined, therapeutically effective amount of therapeutic agent applied to one of the balloons. Thus, there is no need for the clinician to measure and mix the therapeutic agent with other components at the bedside of a patient, which can reduce the procedure time and risk of errors.

BRIEF DESCRIPTION OF THE DRAWINGS

FIG. 5 is a graph plotting data points for elution rate profiles of a bioactive from two different balloon catheter assemblies.

DETAILED DESCRIPTION

Definitions

Figure 1:
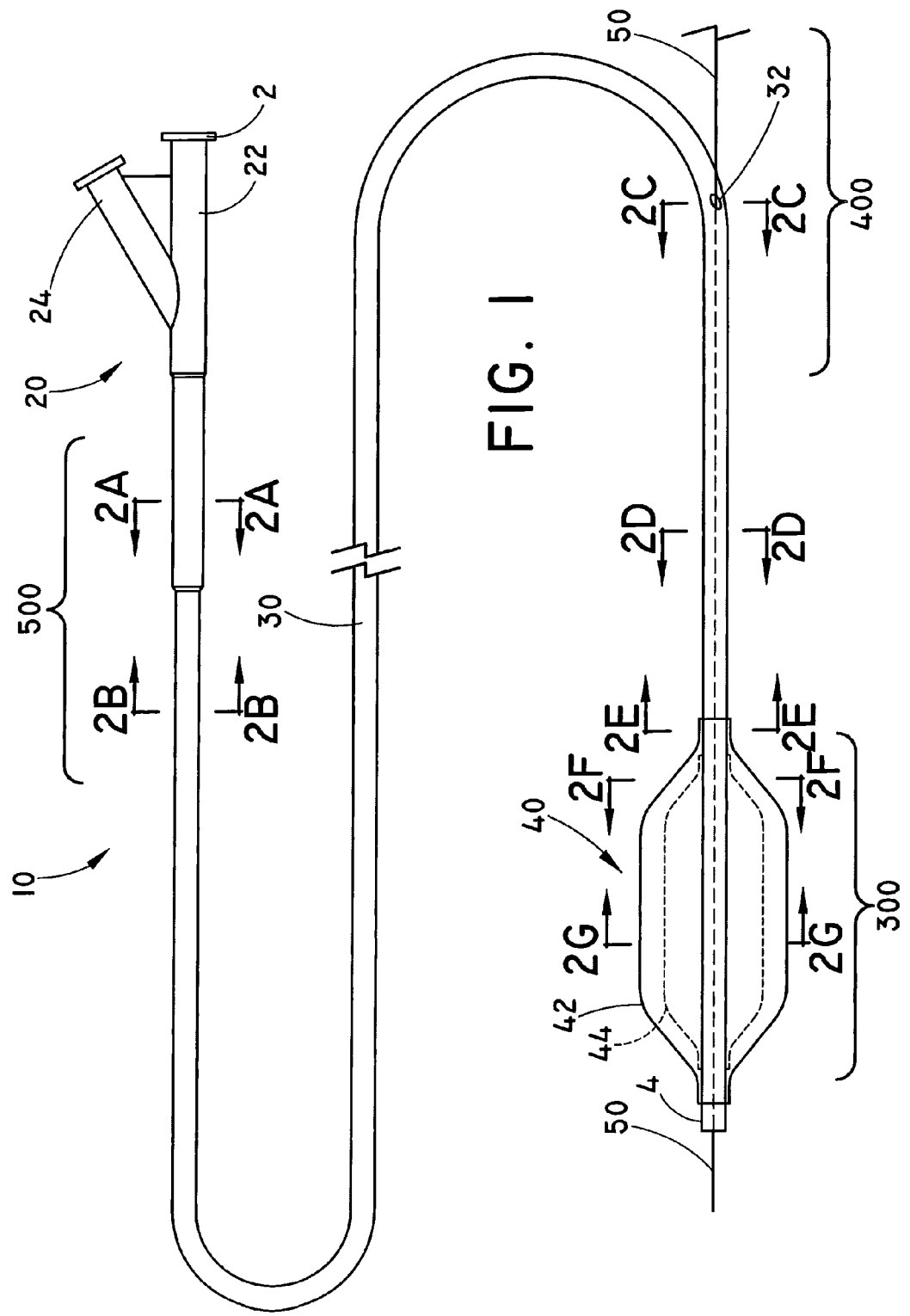
FIG. 1 is a perspective view of a balloon catheter assembly with multiple balloons.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. The materials, methods, and examples disclosed herein are illustrative only and not intended to be limiting.

As used herein the terms "comprise(s)," "include(s)," "having," "has," "can," "contain(s)," and variants thereof, are intended to be open-ended transitional phrases, terms, or words that do not preclude the possibility of additional acts or structures. The present invention also contemplates other embodiments "comprising," "consisting of" and "consisting essentially of," the embodiments or elements presented herein, whether explicitly set forth or not.

The term "biocompatible" material refers to a material that is compatible with living tissue or a living system by not being toxic or injurious and not causing immunological rejection.

The term "biodegradable" material refers to a material that dissipates upon implantation within a body, independent of the mechanisms by which dissipation can occur, such as dissolution, degradation, absorption and excretion. The actual choice of which type of materials to use may readily be made by one of ordinary skill in the art. Such materials are often referred to by different terms in the art, such as "bioresorbable," "bioabsorbable," or "biodegradable," depending upon the mechanism by which the material dissipates. The prefix "bio" indicates that the erosion occurs under physiological conditions, as opposed to other erosion processes, caused for example, by high temperature, strong acids or bases, UV light or weather conditions.

The term "controlled release" refers to the release of an agent at one or more predetermined rate(s). A controlled release may be constant or vary with time. A controlled release may be characterized by a drug elution profile, which shows the measured rate that the agent is removed from a device in a given solvent environment as a function of time. For example, a controlled release elution profile from a medical device may include an initial burst release associated with the deployment of the valve prosthesis, followed by a more gradual subsequent release. A controlled release may be a gradient release in which the concentration of the agent released varies over time or a steady state release in which the agent is released in equal amounts over a certain period of time (with or without an initial burst release).

As used herein, a "barrier layer" is any layer that is placed over at least a portion of a bioactive present in or on a portion of a device of the present invention. In general, the bioactive will not be present in the barrier layer. Any mixing of a bioactive with the barrier layer is unintentional and merely incidental. The barrier layer may or may not be the outer-most layer present on the device. For example, a bioactive may be coated onto a surface of the device, a first barrier layer placed over the bioactive and further barrier layers and layers contain the same or a different bioactive placed on the first barrier layer. The barrier layer may control the release of the bioactive from the device upon implantation.

As used herein, a "carrier" or "carrier material" refers to a material that forms a mixture with bioactive on or in a device of the present invention. The carrier may control and/or enhance the release of the bioactive from the device and into the body. Some carriers enhance the dissolvability of the bioactive and/or the lipophilicity of the bioactive.

As used herein, the term "bioactive" refers to any pharmaceutically active agent that produces an intended therapeutic effect on the body to treat or prevent conditions or diseases. The term bioactive and the term "therapeutic agent" may be used synonymously.

The term "treatment" or "treating" as used herein describes the management and care of a human or veterinary patient for the purpose of combating or preventing a disease, condition, or disorder and includes the administration of a bioactive to alleviate the symptoms or complications, or eliminate the disease, condition, or disorder.

A "therapeutically-effective amount" as used herein is the minimal amount of a bioactive which is necessary to impart therapeutic benefit to a human or veterinary patient. For example, a "therapeutically effective amount" to a human or veterinary patient is such an amount which induces, ameliorates or otherwise causes an improvement in the pathological symptoms, disease progression or physiological conditions associated with or resistance to succumbing to a disorder, for example restenosis.

As used herein and unless otherwise indicated, the term "thermoformable" refers in general to a material that may be reshaped under conditions of temperature and/or pressure. Preferably, a thermoformable polymer may be softened or melted under processing conditions to adhere to adjacent structural components. For example, a catheter shaft assembly may include a thermoformable polymer contacting one or more tubular liners and/or a stiffening member. Upon heat and/or pressurized processing of the catheter shaft assembly, the thermoformable polymer may melt or soften, adhering the tubular liners and/or stiffening member to one another. Preferably, the thermoformable polymer has a flowability above a desired processing temperature, but forms a solid having desired resilience and strength properties at a temperature of intended use (e.g., 37° C. (98.6° F.). The catheter shaft may include a thermoformable polymer that adheres to and fills the voids between structural components therein, such as fluorinated hydrocarbon tubular members and/or a stainless steel stiffening member.

The present disclosure relates to a balloon catheter assembly for delivering a bioactive to a body vessel and methods of treatment using the balloon catheter assembly. For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention generally provides a balloon catheter including an outer perforated balloon, which incorporates at least one bioactive, and an inner balloon. The balloon catheter can be used to dilate treatable regions in a body vessel, such as hardened regions of a stenosis. In one embodiment, the bioactive is present on at least a portion of the outer perforated balloons. In such an embodiment, the bioactive is delivered to the surface of the vessel as a result of the contacting of the outer balloon with the vessel surface.

In other embodiments, a carrier is introduced within the annular space between the inner and outer balloons and released through the perforations of the outer balloon. The carrier preferably changes the elution rate and/or delivery amount of the bioactive to the body. In addition, the carrier can also enhance the representation from within the body using imaging techniques or equipment.

The Balloon Catheter Construction

In a first embodiment, a balloon catheter assembly for delivering a bioactive is provided as shown in FIG. 1. The balloon catheter assembly 10 extends from a proximal end 2 to a distal end 4. Therebetween, the balloon catheter assembly 10 includes manifold 20, a proximal region 500 (further described with respect to FIGS. 2A and 2B) of the catheter shaft 30, an intermediate region 400 (further described with respect to FIG. 2C) of the catheter shaft 30 and a distal region 300 (further described with respect to FIGS. 2E, 2F, 2G, and 3A) of the catheter shaft 30 that includes a multiple balloon assembly 40.

In FIG. 1, the manifold 20 is operatively joined to a catheter shaft 30 in a proximal region 500. The manifold 20 may include a lateral injection port 24 and an inflation port 22. The catheter shaft 30 may also include one or more conventional fittings and/or adapters between the manifold 20 and the proximal end of the catheter shaft 30. The balloon catheter assembly 10 is a "short wire" system (also known as rapid exchange) having a wire guide port 32 within an intermediate region 400 of the catheter shaft 30, providing access to a wire guide lumen extending through the catheter shaft 30 from the wire guide port 32 to the distal end 4 of the catheter shaft 30. Alternatively, the balloon catheter assembly 10 may be an "over the wire" system with the wire guide port 32 positioned proximate the proximal end 2 of the catheter shaft 30 or as part of the manifold 20. That is, the manifold 20 may include the wire guide port 32 in addition to the inflation port 22 and the injection port 24. The distal region 300 of the balloon catheter assembly 10 includes a perforated outer balloon 42 radially disposed around an inner inflation balloon 44. The inner balloon 44 is preferably non-porous and in fluid communication with the inflation port 22 through the body of the catheter shaft 30. The outer balloon 42 is in fluid communication with the injection port 24 through the catheter shaft 30 and separated from both the inner balloon 44 and the inflation port 22. An annular lumen for receiving a bioactive from the injection port 24 may be formed between the inner balloon 44 and the outer balloon 42. Both the inner balloon 44 and the outer balloon 42 may be sealed to the distal end 4 of the catheter shaft 30, within the distal portion 300 of the catheter shaft 30 housing the distal portion of the wire guide lumen. The balloon catheter assembly 10 may be translated over a wire guide 50 shown extending from the wire guide port 32, through the catheter shaft 30 and extending from the distal end 4 of the catheter shaft 30. The balloon catheter assembly 10 is typically provided separately from the wire guide 50, an introducer sheath (not shown) or other devices typically used to insert the balloon catheter assembly 10 within a body vessel.

Figure 1A:
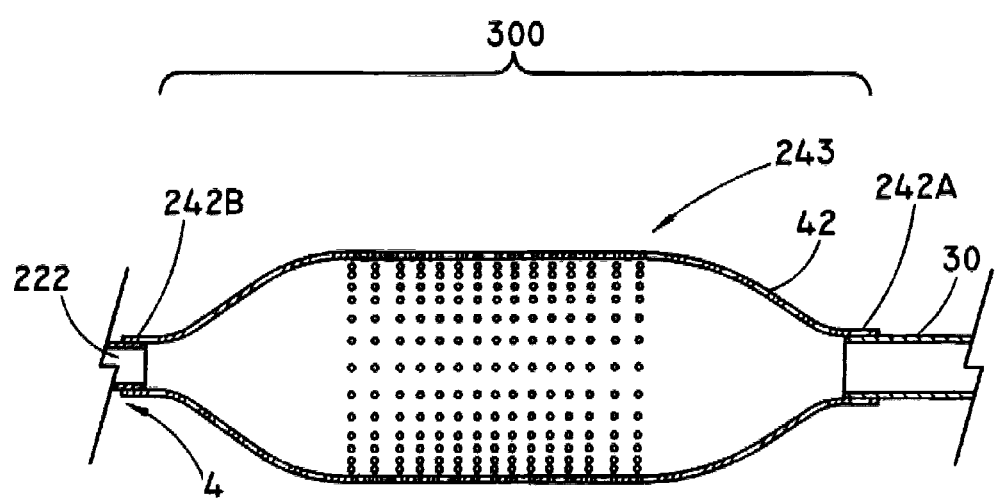
FIG. 1A is a detailed view of a plurality of apertures in the outer balloon surface of the distal portion of the balloon catheter assembly shown in FIG. 1.

The outer balloon 42 may include a means for releasing a fluid, such as a carrier, a bioactive, a contrast media, etc. from the balloon fluid delivery lumen 242. For example in FIG. 1A, the outer balloon 42 may define a plurality of apertures 243 in communication with the balloon fluid delivery lumen 242. FIG. 1A shows a side view of the distal region 300 of the balloon catheter assembly 10, including the proximal seal 242a of the inflated outer balloon 42 to the catheter shaft 30 and the distal seal 242b of the outer balloon 42 to the third tubular member 222. The plurality of apertures 243 can be disposed along a longitudinal portion of the outer balloon 42. Typically, the apertures 243 may have any suitable size and shape, but preferably have at least one dimension between about 10 micrometer (0.0004 inch) and about 1 mm (0.04 inch). The suitable size of the apertures 243 can depend on the desired elution rate of the bioactive, the viscosity of the fluid, the effective time of the procedure, among other considerations known in the art. In another embodiment, the apertures 243 may vary in size, shape, or density to improve the flow characteristics of the fluid being released therethrough. The apertures 243 may be formed by any suitable method including mechanical punching, laser cutting, and the like. Optionally, certain portions of the outer balloon 42 may contain apertures for better localized treatment of the vessel.

In a first aspect of the first embodiment, the catheter shaft 30 is formed from a thermoformable material enclosing one or more tubular members. The tubular members may be formed from a material having a higher melting temperature than the thermoformable material. The tubular members may be secured within the catheter shaft by melting or softening the thermoformable material around the outside of a portion or substantially all of the tubular members, without blocking the lumen extending through each tubular member. Preferably, the tubular members are formed from a fluorinated hydrocarbon, such as PTFE or FEP, or a polyimide. The thermoformable material is preferably a polymer, and may include a polyether block amide (PEBA) polymer or other lower-melting point polymer with a desired level of rigidity and flexibility for forming the catheter shaft 30. The catheter shaft 30 may include tubular members (e.g., 202, 212) having a substantially uniform inner diameter. The wall of the tubular members preferably has a thickness adequate to prevent bursting of the tubular member during inflation and/or delivery of a bioactive fluid. The tubular members are most preferably formed from a fluorinated hydrocarbon, such as poly (tetrafluoroethylene) (PTFE).

Figure 2A:
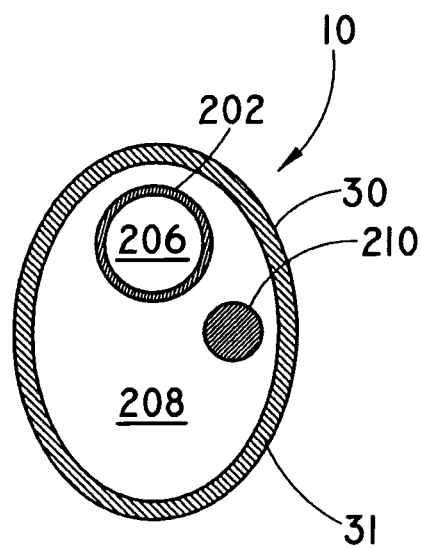
FIG. 2A is a transverse cross-sectional view along line 2A-2A of the balloon catheter assembly shown in FIG. 1.

In a second aspect of the first embodiment, a proximal portion of the catheter shaft 30 may include a stiffening member (210) to improve the pushability of the balloon catheter assembly 10. FIG. 2A is a first cross-sectional view of the catheter shaft 10 along line A-A'. The outer surface of the catheter shaft 30 encloses a first tubular member 202 and a stiffening member 210 positioned within a proximal inflation lumen 208 defined by the inner wall of the catheter shaft 30, proximate the transition from the proximal catheter shaft portion. The first tubular member 202 defines an inflation lumen 206 extending from a proximal end 202a in communication with the inflation port 22 in the manifold 20 to a distal end 202b in communication with the inner balloon 44 at the distal portion 300 of the balloon catheter assembly 10. The stiffening member 210 (as shown in transverse cross section A-A' in FIG. 2A) may be included within a catheter shaft 30 having a wire guide port 32 positioned between the manifold 20 and the distal end 4 of the balloon catheter assembly 10. The stiffening member 210 is preferably sealed within a proximal portion of the catheter shaft 30, rather than being inserted into a lumen of the catheter shaft 30. To enhance the pushability of the balloon catheter assembly 10, the stiffening member 210 is preferably not moveable with respect to the balloon catheter assembly 10. For example, the stiffening member 210 may be integrally formed with the catheter shaft 30 by a thermoformable material 36 that is melted or softened to surround and secure the catheter shaft 30 within the proximal region 500 of the catheter shaft 30 (see, e.g., FIG. 2B). The stiffening member 210 can be formed from any material, and has any suitable dimension, providing a desired level of rigidity to impart a desired level of pushability to the catheter shaft 30 without undesirably reducing the tractability. The stiffening member 210 may be a tapered mandrel having a cross sectional area that decreases in the distal direction along the catheter shaft 30. For example, a stiffening member may be formed from a 0.038 mm (0.015-inch) diameter proximal end tapered to a distal end with a diameter of about 0.05 mm (0.002-inch). Examples of suitable stiffening member materials include stainless steel, nickel-titanium alloy, cobalt-chromium alloy, and stiff polymers such as poly(tetrafluoroethylene) (PTFE), high density polyethylene (HDPE) and polyether ether ketone (PEEK), and other rigid materials. U.S. Publication 2006/0258987A1, published Nov. 16, 2006, which is incorporated herein by reference in its entirety, describes another example of a stiffening member construction suitable for use within the catheter shaft 30.

Referring to FIG. 2A, the catheter shaft 30 may be formed from any suitable material, but preferably includes a thermoformable material 36. The catheter shaft 30 may comprise an outer sleeve 31 formed as an extruded sleeve, shrink tube, extruded over-jacket, or dip coat. The catheter shaft 30 is preferably a thermoformable material 36 and may comprise polymers, for example, HDPE, PTFE, PET, polyester or PEBA, polyurethane, polyimide, polyolefin, nylon, or any combination thereof. The catheter shaft is preferably formed of a PEBA polymer outer sleeve 31 enclosing the tubular members 202, 212, 222. The outer sleeve 31 may be applied by, for example, over-extrusion, dip-coating, melt fusion, or heat shrinking. For example, the outer sleeve 31 may be a PET shrink tube. The type of material may also be selected to complement other catheter components; for example, a nylon sleeve may bond and interact better with a nylon expandable member such as a balloon or basket and/or a nylon wire guide lumen. Selection of coating materials and diameter allow manipulation of the shore hardness of the catheter shaft 30, which offer the desired functional properties.

The balloon catheter assembly 10 may be configured with a desirably small outer diameter, a sufficiently flexibility to pass through a tight curvature or tortuous passageway, and a pushability, tractability, and/or traceability sufficient to be navigated through such tightly curved and/or tortuous pathways in the similar manner as a wire guide. A preferred outer diameter will be different for different applications, but the outer diameter a catheter embodiment configured for use in peripheral blood vessels may be in the range of about 1.0-1.4 mm (0.040-0.055 inches), and the outer diameter may differ along the length of the catheter embodiment. As mentioned previously, the catheter shaft 30 may optionally be configured as a rapid exchange catheter, as shown in FIG. 1. The outside diameter of the catheter shaft 30 is typically approximately 1-1.5 mm (0.04-0.059 inches). A preferred catheter shaft 30 tapers from a greater proximal outer diameter (such as, for example, about 1.2 mm (0.048 inches) to about 1.3 mm (0.052 inches) to a lesser (reduced) distal diameter (such as, for example, about 1.1 mm (0.044 inches) to about 1.0 mm (0.040 inches). The lesser distal diameter may present improved tractability and/or traceability for navigation of tortuous passages.

The non-balloon portion of the catheter shaft 30 may optionally include a coating on the outer sleeve 31. A preferred coating may provide a desirable lubricity profile that exhibits low friction during introduction of the device through, for example, a blood vessel. A preferred coating may also enhance the fluid-tight seal of the catheter shaft with the body vessel. The fluid-tight seal may be configured to prevent leakage of pressurized inflation fluid (for example, at pressures in a normal operating range up to about 0.8-1.4 MPa (8-14 atm), and preferably configured to prevent leakage at pressures exceeding normal ranges, for example, up to or exceeding about 2.7 MPa (27 atm)). The coating may be a thermoplastic polymer such as, for example, a polyester or PEBA.

Figure 2B:
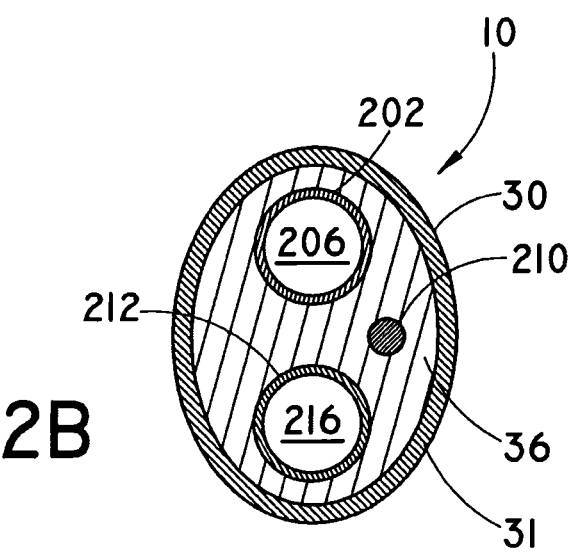
FIG. 2B is a transverse cross-sectional view along line 2B-2B of the balloon catheter assembly shown in FIG. 1.

FIG. 2B is a second transverse cross-sectional view of the catheter shaft 10 along line B-B' in FIG. 1, positioned longitudinally distal to line A-A'. A second tubular member 212 defining a fluid delivery lumen 216 is positioned within the catheter shaft 30, beside the first tubular member 202 and stiffening member 210 described above. The fluid delivery lumen 216 extends from a proximal end 212a attached to the manifold 20 to a distal end 212b in communication with an annular balloon fluid delivery lumen 242 inside the outer balloon 42.

A thermoformable material 36 is placed or injected to fill the body of the catheter shaft between the tubular members (202, 212), the stiffening member 210 and an outer sleeve 31. Preferably, the second tubular member 212 is similar to the first tubular member 202, except that the proximal end of the second tubular member 212 is positioned distal to the proximal end of the first tubular member 202. The stiffening member 210 in FIG. 2B may have a smaller cross-sectional area than in FIG. 2A, due to tapering of a distal portion of the stiffening member 210 in the distal longitudinal direction. Alternatively, the tapering of the stiffening member 210 may begin distal to the cross-section of FIG. 2B and proximal to FIG. 2C.

Preferably, the inflation lumen 206 and the fluid delivery lumen 216 of the tubular members remain oriented side-by-side and substantially parallel to one another for at least a portion of the catheter shaft 30. The first tubular member 202 and the second tubular member 212 may be formed from the same or similar material and may have similar or identical inner diameters (e.g., about 0.36 mm (0.014-inch)) and thicknesses (e.g., about 0.064 mm (0.0025-inch)).

In one example, to form the catheter shaft 30, the first tubular member 202 and the second tubular member 212 may be placed within each of the two lumens of a dual lumen thermoplastic sleeve. The dual lumen thermoplastic sleeve is formed from a thermoformable material 36 and has a "figure 8" transverse cross section defining two lumens. The two lumens may have a wall thickness of at least about 0.064 mm (0.0025 inches) between the two lumens. Optionally, while being inserted into the thermoplastic sleeve, each of the tubular members 202, 212 may be supported within the thermoplastic sleeve lumens on separate temporary mandrels. The thermoplastic sleeve lumens may have any suitable inner diameters to receive the tubular members 202, 212, such as between about 0.38 mm (0.015 inches) and 0.51 mm (0.020 inches).

Optionally, the thermoplastic sleeve may include a first lumen and a second lumen with substantially identical inner diameters. Alternatively, the thermoplastic sleeve may include a first lumen with an inner diameter of about 0.38 mm (0.015 inches) and a second lumen with an inner diameter of about 0.46-0.64 mm (0.018-0.025 inches). Both lumens within the thermoplastic sleeve are preferably substantially parallel to one another and extend along the entire length of the thermoplastic sleeve. The dual-lumen thermoplastic sleeve may be constructed of a thermoformable material 36 such as, for example, a polyolefin, polyester or PEBA, or other appropriate polymeric material that may be heated to flow around and join together the tubular members 202, 212 within the lumens of the thermoplastic sleeve to the stiffening member 210 and a third tubular member 222 positioned adjacent the thermoplastic sleeve (i.e., external to the lumens of the thermoplastic sleeve but within the outer sleeve 31).

As indicated above, to further improve pushability, tractability, and/or traceability of the balloon catheter assembly 10, the stiffening member 210 is preferably integrally joined to the tubular members 202, 212 alongside the thermoplastic sleeve. The stiffening member can have the tapered distal end disposed distal (e.g., 5 cm) to the wire guide port 32. Preferably, the stiffening member 210 is not inserted through a lumen within the thermoplastic sleeve, but rather, is integrally formed within the catheter shaft after heat processing of the thermoplastic sleeve. The can permit the thermoformable material 36 to flow around the stiffening member 210 and the tubular members 202, 212, 222 during processing to form a single catheter shaft after heat and/or pressure processing. The stiffening member 210 may be positioned outside the thermoplastic "FIG. 8" sleeve but inside the outer sleeve 31. The outer sleeve 31 may be formed of any suitable heat-shrinkable material that is capable of forming a secure bond with the dual-lumen thermoplastic sleeve and/or one or more of the tubular members 202, 212, 222.

The catheter shaft 30 may be formed by enclosing the dual-lumen thermoplastic sleeve having the "figure-8" cross-section defining a first lumen and a second lumen and the stiffening member 210 within the outer heat-shrinkable sleeve. A heat shrinkable outer sleeve 31 may be placed around the thermoplastic sleeve, the tubular members 202, 212, 222 and the stiffening member 210. The outer sleeve 31 typically has a higher melting point than that of the thermoformable material 36 of the thermoplastic sleeve. When the thermoplastic sleeve comprises a nylon or PEBA, a preferred outer sleeve 31 material comprises a copolymer, and more preferably, a block copolymer such as a cross-linked PEBA. Block copolymers comprise alternating segments formed of a harder, or more crystalline material, and a softer, or more amorphous, material. When the copolymer is PEBA, the harder material comprises a polyamide, such as nylon 12, and the amorphous segments comprise polyether. The hard and the amorphous segments are linked together by urethane groups in known fashion. By varying the ratio of the polyamide to polyether blocks, PEBA compositions of varying properties, such as melting point, dimensional stability, hardness, etc., may be created. Commercially available grades of PEBA typically have a Shore hardness between about 72D and 75A. Higher polyamide to polyether ratios will result in a higher Shore hardness (stiffer material), and lower polyamide to polyether ratios result in a lower Shore hardness (softer material).

Typically, the outer sleeve 31 comprises a thermoplastic material that is subjected to at least partial cross-linking. The thermoformable material 36 is preferably free of crosslinking or has a reduced degree of cross linking compared to the outer sleeve 31. When a polymeric material is cross-linked, chemical links are established between the molecular chains of the polymer, thereby resulting in a change of properties in the cross-linked material when compared to the non-cross-linked material. In general, when a material is cross-linked, the properties of the cross-linked material cause it to behave more in the nature of a thermoset material. Thus, the resulting material may have higher dimensional stability (hoop strength), higher tensile strength, higher stiffness and density, higher melting temperature, improved heat memory, improved chemical resistance, and improved physical strength, among other properties, when compared to the non-cross-linked thermoplastic. Similarly, some properties, such as elongation and the ability to flex, are generally lower in the cross-linked material when compared to the non-cross-linked material. Thus, for example, when the cross-linked material is a block copolymer such as PEBA, the properties of the resulting cross-linked material will generally differ from those of the original block copolymer in the manner described above. It is often desirable to control the amount, or degree, of cross-linking of a particular block copolymer in order to optimize the desired properties of the cross-linked polymer. In some instances a trade-off must be made to arrive at a copolymer that is sufficiently cross-linked to be effective for its intended purpose, but not so highly cross-linked as to effectively negate the beneficial results of the cross-linking.

The outer sleeve 31 preferably includes a cross-linked PEBA polymer, while the thermoformable material 36 is preferably a non-cross-linked PEBA polymer. Cross-linking procedures are well known in the arts. Typically, cross-linking is initiated by chemical means, or by irradiation. With chemical initiation, an initiating compound, such as peroxide, is mixed into the matrix of the polymer. With irradiation, a material is exposed to high-energy radiation to initiate the formation of the molecular bonding. Both of these methods have been found to effectively promote molecular bonding within the material. In modern practice, irradiation is probably the more common mode for initiating the cross-linking reaction. Examples of procedures involving the cross-linking of polymeric compositions for use in medical applications are discussed, e.g., in U.S. Pat. Nos. 6,663,646 and 6,596,818, both of which are incorporated herein by reference in their entirety. The outer sleeve may include other cross-linkable polymers, with or without PEBA. A copolymer may be formed of alternating hard blocks and amorphous blocks. Similarly, the copolymer may be selected such that following cross-linking, the copolymer has a sufficient number of non-cross-linked active sites (analogous to the amide sites on the PEBA copolymer) that are capable of forming a secure bond with the adjoining inner layer of the sheath. A non-limiting list of other polymeric compositions that may be utilized as an outer heat shrink layer under appropriate conditions includes polyolefins, PET and FEP.

The assembly of the tubular members, the dual-lumen thermoplastic sleeve and the outer heat-shrinkable sleeve can be joined together by heating a catheter assembly to a temperature suitable to melt or soften the thermoformable material 36 and shrink the outer sleeve 31, but below a temperature effective to melt or soften the tubular members 202, 212. Upon exposure to a controlled amount of heat, the thermoformable material 36 may melt and flow between the interstices within the outer sleeve 31, and is fused to the outer surfaces of the tubular members 202, 212, 222 and the stiffening member 210. The outer sleeve 31 may compress the thermoformable material 36, the tubular members 202, 212, 222 and the stiffening member 210 together to form the catheter shaft 30 in a conventional manner when heat shrink techniques are used to form the catheter shaft 30. Those skilled in the art will appreciate that the outer sleeve 31 and a polymeric thermoformable material 36 may be formed from a variety of medical grade materials suitable for such purposes, so long as the layers are capable of being fused or otherwise bonded or securely attached to each other upon the application of heat, as described. The temperature may vary widely, depending on material. Polyolefin has a low shrink temperature of about 290° F. (143° C.); however it can withstand temperatures up to about 450° F. (232° C.). PET shrinks at 302° F. (150° C.) but melts at 374° F. (190° C.). PEBA shrinks at 340° F. (171° C.) and will not degrade at temperatures under about 500° F. (260° C.). FEP shrinks at 375° F. (190° C.), but does not degrade until temperatures exceed 600° F. (315° C.). For example, the catheter assembly may be heated to a temperature of about 400-550° F. (204-288° C.) and preferably about 500° F. (260° C.), to join the dual-lumen sleeve comprising the thermoformable material 36, the two tubular members 202, 212 and the stiffening member 210 within the heat-shrinkable outer sleeve 31 to form the balloon catheter assembly 10. If present, the temporary mandrels may be removed from the lumens of the tubular members 202, 212 after heat processing to join the assembly together. Optionally, the assembly may be heated while enclosed in a suitable bonding sleeve, such as an FEP heat shrink material, to provide heat-transmitting contact to the outer sleeve 31 during processing. The bonding sleeve may later be removed along with any temporary mandrels within the tubular members 202, 212.

The balloon catheter assembly 10 is preferably configured as a "short-wire" configuration, where the wire guide lumen 226 may not extend the entire length of the catheter shaft 30. In this type of catheter, the wire guide lumen may extend only from the distal end 4 of the balloon catheter assembly 10 to a point intermediate the distal end 4 and manifold 20 at the proximal end of the catheter shaft 30. The shorter guide wire lumen 226 facilitates the exchange a first balloon catheter assembly 10 for other medical devices, such as a second catheter (e.g., to "exchange out" a balloon catheter, and then "exchange in" a stent-deployment catheter). Referring to FIG. 1, the exchange is preferably executed by leaving a wire guide 50 in place during removal of the first catheter and using it as a guide for the second catheter. The first catheter is withdrawn or otherwise removed over the wire guide 50, and then a second catheter is introduced over the wire guide.

Referring to FIG. 2B, the third tubular member 222 is preferably integrally joined to the stiffening member 210 and the other tubular members 202, 212 within at least the portion of the catheter shaft 30 distal to the wire guide port 32 by the thermoformable material 36 within the outer sleeve 31. Preferably, the stiffening member 210 is not inserted through a lumen within the catheter shaft, but rather, is integrally formed within the catheter shaft after heat processing of the thermoplastic sleeve to flow around the stiffening member 210 and the tubular members 202, 212, 222 to form a single catheter shaft.

Figure 2C:
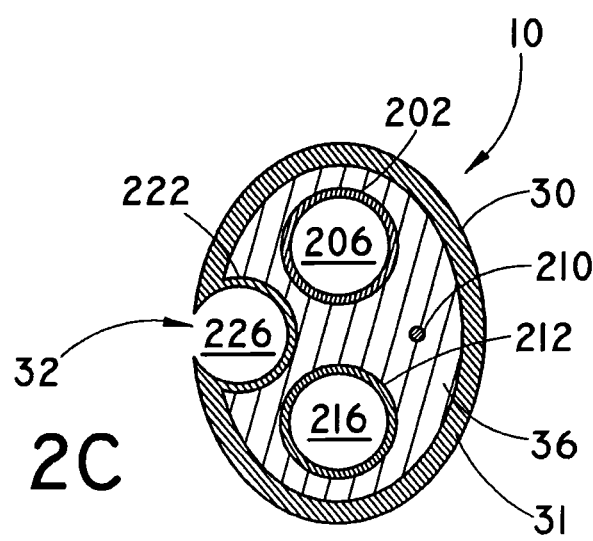
FIG. 2C is a transverse cross-sectional view along line 2C-2C of the balloon catheter assembly shown in FIG. 1.

FIG. 2C is a third transverse cross-sectional view of the catheter shaft 10 along line C-C', positioned longitudinally distal to line B-B' at the wire guide port 32. In order to facilitate use of the balloon catheter assembly 10 in a short wire (i.e., "rapid exchange") configuration, a wire guide port 32 is provided at the proximal end 222a of the third tubular member 222. A third tubular member 222 defining a wire guide lumen 226 in communication with the wire guide port 32 is positioned within the catheter shaft 30. A proximal end of the third tubular member 222 may be in communication with the wire guide port 32 and a distal end may be proximate the distal end 4 of the catheter shaft 30. The wire guide port 32 may be formed by skiving an opening through the catheter shaft 30 to allow a wire guide 50 to pass through a portion of the balloon catheter assembly 10. Translating the balloon catheter assembly 10 along a wire guide 50 in this manner may facilitate rapid introduction and/or exchange of the balloon catheter assembly 10 along the wire guide 50. The third tubular member 222 is positioned beside the first tubular member 202, the second tubular member 212 and stiffening member 210 described above. Preferably, the third tubular member 222 is adapted to slidably receive a wire guide through the wire guide port 32. In an "over the wire" system, the proximal end of the third tubular member 222 may be in communication with the wire guide port 32 disposed proximate the proximal end 2 of the catheter shaft 30, while the distal end of the third tubular member 222 may be proximate the distal end 4 of the catheter shaft 30.

Referring to FIG. 2C, the third tubular member 222 may be formed from a material having sufficient durability and a desirably low amount of friction. The wall of the third tubular member 222 will also preferably have sufficient structural strength and/or rigidity to prevent the wires of the wire guide 50 from protruding through the wall of the third tubular member 222. For example, the third tubular member 222 may be formed from PTFE having a thickness of about 0.033 mm (0.0013 inches) and an inner diameter of about 0.46 mm (0.018 inches) inner diameter to receive the wire guide. The third tubular member 222 may be adapted to bind to a thermoformable material 36 within the catheter shaft 30, for example by roughening the outer surface of the material. The stiffening member 210 in FIG. 2C may have a smaller cross-sectional area than in FIG. 2B, due to tapering of the stiffening member 210 in the distal direction. The third tubular member 222 may be formed of a lubricious material. Lubricious inner liners for sheaths are well known in the medical arts, and those skilled in the art can readily select an appropriate liner for a particular use. The lubricous material provides a slippery inner surface for easy translation of a wire guide 50 through the wire guide lumen 226 extending longitudinally through the interior of third tubular member 222.

Preferably, the radially outer surface of one or more of the tubular members 202, 212, 222 is roughened in any conventional manner, such as by chemical etching, to form a rough outer surface to facilitate bonding with a dual-lumen thermoplastic sleeve and/or a heat-shrinkable (thermoset) outer sleeve 31 as described above.

In one example, the third tubular member 222 may be incorporated into the balloon catheter assembly 10 by placing the third tubular member 222 adjacent to and alongside the dual-lumen thermoplastic "figure 8" sleeve formed from a thermoformable material 36 enclosing the first tubular member 202 and the second tubular 212, described above. The third tubular member 222 may be placed with its proximal end 222a overlapping with the distal end of the tapered stiffening member 210 within the outer heat-shrinkable sleeve. Upon heating the assembly, the thermoplastic sleeve and the outer heat shrinkable sleeve join the first tubular member 202, the second tubular member 212, the third tubular member 222 and the stiffening member 210 together to form the catheter shaft 30. The wire guide port 32 may be formed by cutting away an aperture in the outer sleeve 31 to access the proximal end 222a of the wire guide lumen 226 within the third tubular member 222. The distal end 222b of the wire guide lumen 226 may form the distal end 4 of the catheter shaft 30.

Figure 2D:
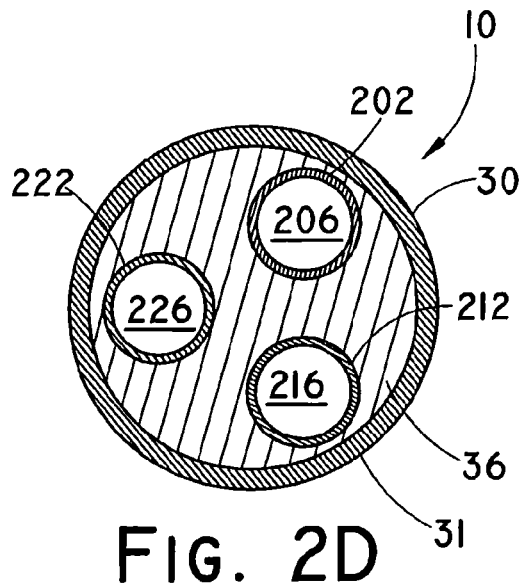
FIG. 2D is a transverse cross-sectional view along line 2D-2D of the balloon catheter assembly shown in FIG. 1.

FIG. 2D is a fourth transverse cross-sectional view of the catheter shaft 10 along line D-D', longitudinally distal to line C-C' between the wire guide port 32 and the distal region 300 of the balloon catheter assembly 10. The catheter shaft 30 encloses the first tubular member 202, the second tubular member 212 and the third tubular member 222 defining the inflation lumen 206, the fluid delivery lumen 216 and the wire guide lumen 226 (respectively) in a side-by-side orientation. The distal end of the stiffening member 210 is also shown, which preferably extends from the manifold 20 to a distal end positioned distal (e.g., 5 cm) to the wire guide port 32.

Figure 2E:
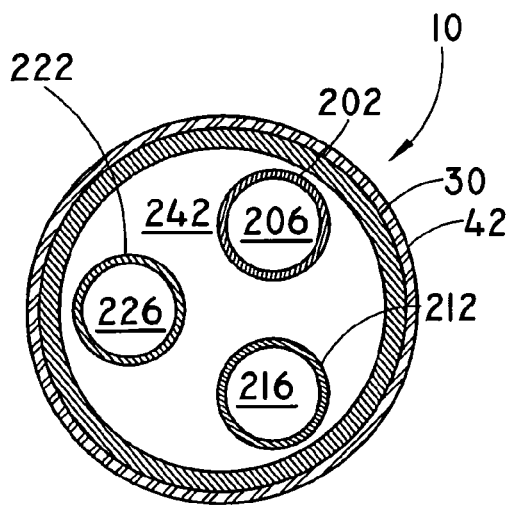
FIG. 2E is a transverse cross-sectional view along line 2E-2E of the balloon catheter assembly shown in FIG. 1.

FIG. 2E is a fifth transverse cross-sectional view showing the distal region 300 of the balloon catheter assembly 10 along the catheter shaft 30 at line E-E', longitudinally distal to line D-D', at the distal end 212b of the second tubular member 212. The outer balloon 42 defines an annular balloon fluid delivery lumen 242 extending radially between the outer balloon 42 and the inner balloon 44 and extending longitudinally from a proximal seal 242a to a distal seal 242b. The outer balloon 42 is sealed at the proximal seal 242a around the catheter shaft 30, enclosing the first tubular member 202, the second tubular member 212 and the third tubular member 222. The proximal seal 242a may be positioned proximal to the distal end 212b of the second tubular member 212 and is in fluid communication with the fluid delivery lumen 216. The first tubular member 202 enclosing the inflation lumen 206 and the third tubular member 222 enclosing the wire guide lumen 226 preferably remain in side-by-side orientation enclosed by the outer balloon 42.

Figure 2F:
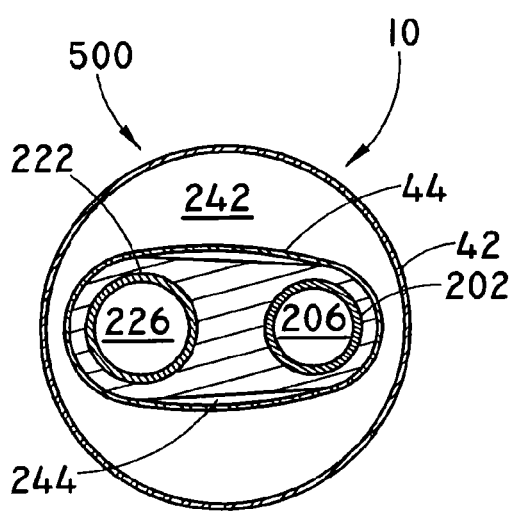
FIG. 2F is a transverse cross-sectional view along line 2F-2F of the balloon catheter assembly shown in FIG. 1.

FIG. 2F is a sixth cross-sectional view showing the distal region 300 of the balloon catheter assembly 10 along line F-F', longitudinally distal to line E-E', at the distal end 202b of the first tubular member 202. The inner balloon 44 defines a balloon inflation lumen 244 extending radially around the third tubular member 222 passing therethrough, and extending longitudinally from a proximal seal 244a to a distal seal 244b. The inner balloon 44 is sealed at the proximal seal 244a around the first tubular member 202 and the third tubular member 222. The proximal seal 244a is positioned proximal to the distal end 202b of the first tubular member 202 and is in fluid communication with the inflation lumen 206. The annular balloon fluid delivery lumen 242 is shown between the outer balloon 42 and the inner balloon 44.

Figure 2G:
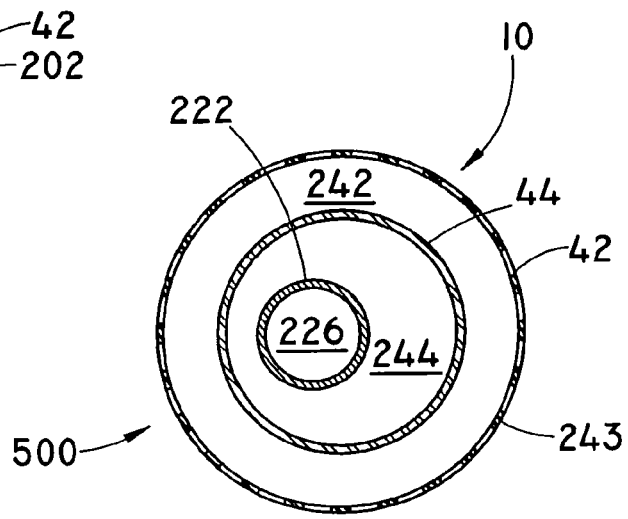
FIG. 2G is a transverse cross-sectional view along line 2G-2G of the balloon catheter assembly shown in FIG. 1.

FIG. 2G is a seventh cross-sectional view showing the distal region 300 of the balloon catheter assembly 10 along line G-G', longitudinally distal to line F-F', positioned between a proximal seal 244a and a distal seal 244b of the inner balloon 44. The outer balloon 42 is coaxially disposed around the inner balloon 44, defining the balloon fluid delivery lumen 242 in communication with the fluid delivery lumen 216. The inner balloon 44 defines the balloon inflation lumen 244 in communication with the inflation lumen 206 and separated from the wire guide lumen 226 by the third tubular member 222. The outer balloon 42 includes the plurality of apertures 243.

Figure 3A:
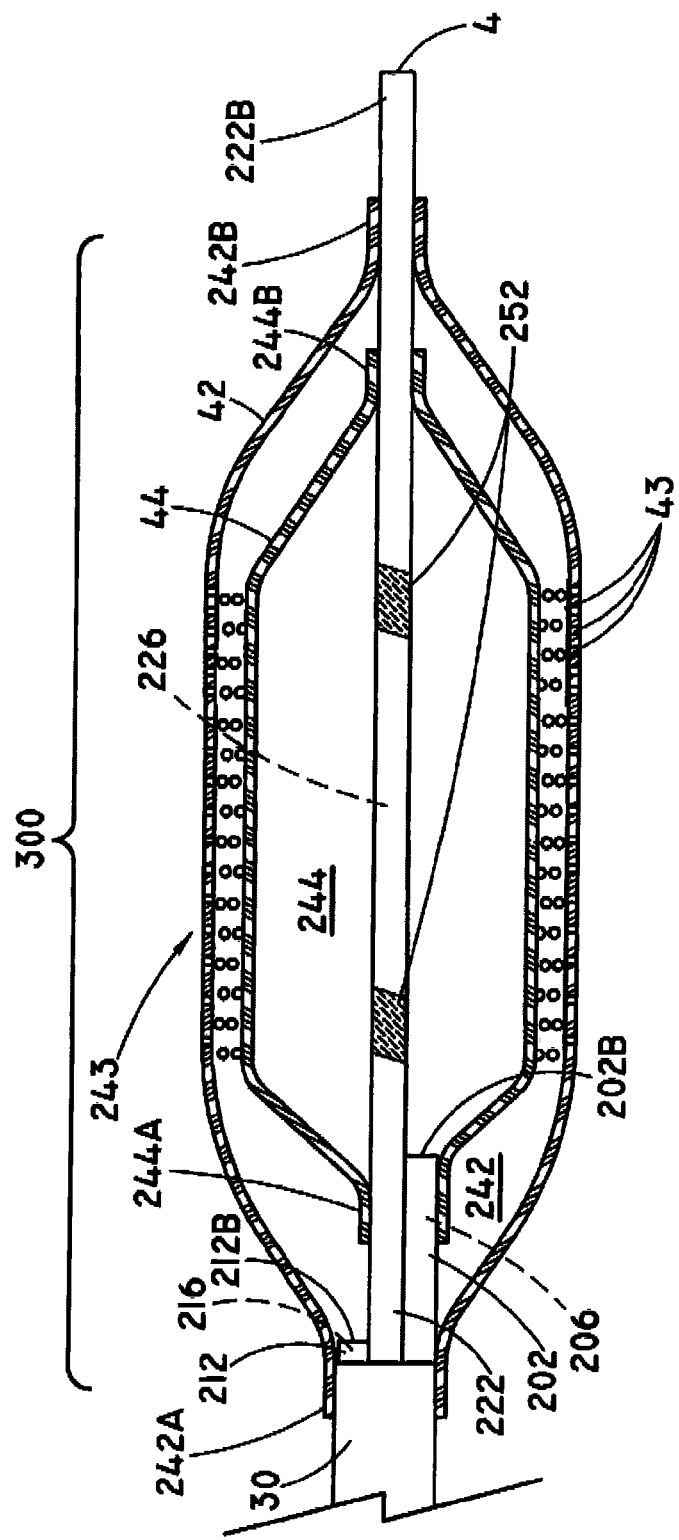
FIG. 3A is a longitudinal cross sectional view of the distal portion of a balloon catheter assembly having multiple balloons.

FIG. 3A is a longitudinal cross-sectional view of the distal region 300 of the balloon catheter assembly 10. The catheter shaft 30 encloses the first tubular member 202, the second tubular member 212 and the third tubular member 222 in a side-by-side configuration. The proximal seal 242a joins the outer balloon 42 to the catheter shaft 30 proximal to the distal end 212b of the second tubular member 212 and the proximal seal 244a of the inner balloon 44. The outer balloon 42 is disposed circumferentially around the inner balloon 44, defining the balloon fluid delivery lumen 242 extends longitudinally from the proximal seal 242a to the distal seal 242b around the third tubular member 222. An inner balloon 44 proximal seal 244a joins the inner balloon 44 around both the first tubular member 202 and the third tubular member 222, proximal to the distal end 202b of the first tubular member 202. The inner balloon 44 is disposed circumferentially around the third tubular member 222 and defines the balloon inflation lumen 244 extending longitudinally from the proximal seal 244a to the distal seal 244b around the third tubular member 222. Preferably, the distal seal 242b may overlap or be positioned around the distal seal 244b. Alternatively, the distal seal 244b of the inner balloon 44 is positioned proximal to the distal seal 242b of the outer balloon 42. Optionally, additional thermoformable material may be placed between the distal end 202b of the first tubular member 202 and the third tubular member 222.

The inner balloon 44 and the outer balloon 42 may be formed from a semi-compliant expandable material. Preferably, the inner balloon 44 and the outer balloon 42 are formed from the materials having a similar Young's modulus and expandability. For example, the balloons may be formed from a polyamide (e.g., nylon 12) material, PEBA and blends thereof (e.g., nylon 12/PEBA and PEBA/PEBA blends). Alternative materials include polyolefins, polyolefin copolymers and blends thereof; polyesters (e.g., poly(ethylene terephthalate), PET); polyurethane copolymers with MDI, HMDI or TDI hard segment and aliphatic polyester, polyether or polycarbonate soft segment (e.g., Pellethane, Estane or Bionate); and polyester copolymers with 4GT (PBT) hard segment and aliphatic polyester or polyether soft segments (e.g., Hytrel, Pelprene or Arnitel).

The proximal seal and distal seal of each balloon (242a, 242b, 244a, 244b) may be formed in any suitable manner. Typically, the proximal and distal inner surfaces of the balloons 42, 44 are sealably attached to the catheter shaft 30 or a tubular member, as described above. Means of sealing the balloons 42, 44 include, for example, heat sealing, using an adhesive to form the seal, forced convection heating, radio frequency heating, ultrasonic welding, and laser bonding. Shrink tubing may be used as a manufacturing aid to compress and fuse the balloon 42, 44 to the catheter shaft 30 or a tubular member 202, 212, 222. The shrink tubing may be removed and disposed of after the balloon 42, 44 is sealed, or may remain on as part of the connected structure. If the catheter shaft 30 has an outer coating, the balloon 42, 44 may be bonded to the coating or directly to the catheter shaft 30.

When configured for use in a peripheral blood vessel, the inflated diameter of the outer balloon 42 may be about 1.5 mm (0.059 inches) to about 8 mm (0.3 inches), while a catheter intended for coronary vascular applications preferably has an expandable portion 14 with an inflated diameter range of from about 1.5 mm (0.059 inches) to about 4 mm (0.2 inches). When configured for use in bile ducts, the expanded diameter of the outer balloon 42 may be about 5-15 mm (0.2-0.59 inches) with a length of approximately 15-60 mm (0.59-2.4 inches) and up to 200-250 mm (7.9-9.8 inches), and the outer diameter of the catheter shaft 30 may be up to about 3.5 mm (0.14 inches). The catheter shaft may be about 3-12 French between proximal to the balloons (i.e., an outer diameter of about 1 mm-4 mm (0.04-0.16 inches)), and preferably about 4-8 French.

Optionally, the balloon catheter assembly 10 may include radiopaque material to provide a means for locating the balloon catheter assembly 10 within a body vessel. For example, the third tubular member 222 may include one or more marker bands 252 annularly disposed around the outside of the third tubular member 222 within the inner balloon 44. If desired, radiopaque bands 252 may be added to the third tubular member 222. Radiopaque marker bands 252 may be used by a clinician to fluoroscopically view and locate the distal portion 300 of the balloon catheter assembly 10 at a treatment site within a body vessel. Various configurations of radiopaque marker bands 252 may be used. For example, radiopaque marker band 252 may be located on a distal end 4 and/or on the third tubular member 222 within the inner balloon 44. As shown, the radiopaque marker bands 252 may be stripes. Such radiopaque markers may be constructed by encapsulating a radiopaque material, such as a metallic ring, within the material of catheter shaft. Alternatively a portion of the catheter shaft may be made radiopaque for example by constructing the portion from a radiopaque polymer. For example a polymer may be mixed with a radiopaque filler such as barium sulfate, bismuth trioxide, bismuth subcarbonate or tungsten. The radiopaque material can comprise any suitable opacifying agent, further including bismuth, tantalum, or other suitable agents known in the art. The concentration of the agent in the coating may be selected to be adequately visible under fluoroscopy.

An "over the wire" system may still be used. The catheter shaft may include one or more tubular members defining at least one of the inflation lumen, the fluid delivery lumen, and the wire guide lumen. The stiffening member, as described above, may also be included in the catheter shaft. The "over the wire" system has the wire guide port positioned as part of the manifold, and may include the inflation port and the injection port. The balloon catheter assembly may be translated over the wire guide extending from the wire guide port, through the catheter shaft and extending from the distal end of the catheter shaft. Other features, such as the method of making the catheter shaft, the varying of the aperture size or frequency, are described in U.S. PCT Application Number US2008/75970 filed on Sep. 11, 2008, incorporated herein by reference in its entirety.

Bioactives

Figure 4A:
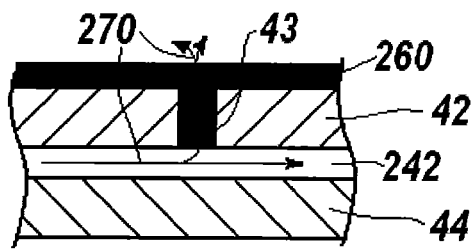
FIGS. 4A-4E are enlarged cross sectional views of a portion of a balloon catheter assembly, depicting various embodiments of bioactive layers and other layers.
Figure 4B:
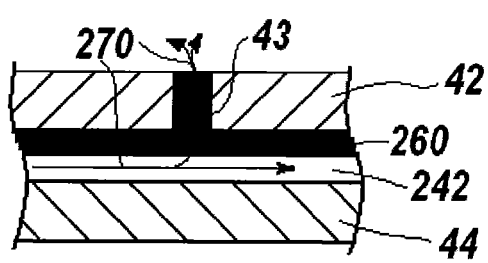
Figure 4C:
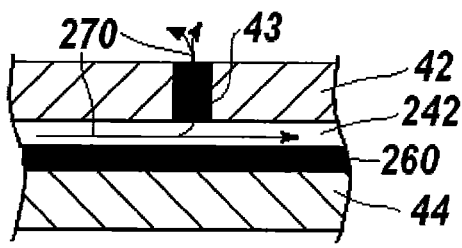

At least one of the balloons is associated with a first composition comprising one or more bioactives 260, preferably along a surface of a balloon or incorporated within the material of a balloon. In FIG. 4A, the bioactive 260 is shown coated directly on the exterior surface of the outer balloon 42. The annular lumen 242 is shown between the inner balloon 44 and the outer balloon 42. A carrier 270, described in more detail below, is depicted traversing through the annular lumen 242 and exiting out of the aperture 43 of the outer balloon. Alternatively, the bioactive 260 can be coated along the interior surface of the outer balloon 42 (FIG. 4B) or along the exterior surface of the inner balloon 44 (FIG. 4C). The embodiments in FIGS. 4B-4C permit the outer balloon 42 to serve as a barrier between the vessel wall and the bioactive. It is particularly useful when duration of the navigation of the balloon catheter is unknown or difficult and it is desirable to control the release of bioactive. While the bioactive is shown in the figures as applied to only one surface of the balloon, it can be appreciated by those skilled in the art that one or more bioactives can be applied to more than one of the surfaces of the outer and inner balloons or all of the surfaces of the inner and outer balloons, namely the outer surface of the inner and outer balloons and the inner surface of the outer balloon. The bioactive 260 may be applied to the balloon by spraying, dipping, pouring, pumping, brushing, wiping, vacuum deposition, vapor deposition, plasma deposition, electrostatic deposition, ultrasonic deposition, epitaxial growth, electrochemical deposition or any other method known to those skilled in the art.

Figure 4D:
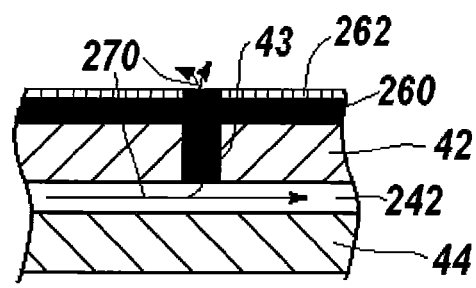

In another embodiment, the bioactive is coated onto the balloon and one or more barrier layers are placed over at least a portion of the bioactive. In FIG. 4D, the bioactive 260 is shown coated directly on the exterior surface of the outer balloon 42, and the barrier layer 262 is applied on top of the bioactive 260. The barrier layer 262 may also be similarly applied to the bioactive layer in the embodiments of FIGS. 4B and 4C as appreciated by those skilled in the art. In this instance, a carrier can be introduced, for example through the apertures of the outer balloon, which is adapted to deactivate, wash away, and/or dissolve the barrier layer 262 in order to permit the release of the bioactive 260. The barrier layer 262 may be particularly useful when duration of the navigation of the balloon catheter is unknown or difficult and it is desirable to control the release of bioactive.

In another embodiment, the bioactive 262 is mixed with a carrier material (not shown) and this first composition mixture is applied to the surface of the balloon. In such a configuration, the release of the bioactive may be dependent on factors including the composition, structure and thickness of the carrier material. In yet another embodiment with the bioactive mixed with a carrier material and applied to the balloon, the carrier material may be applied to the surface of the balloon and the bioactive absorbed into the carrier material. In one embodiment, the carrier material may contain pre-existing channels, through which the bioactive may diffuse, or channels created by the release of the bioactive, or another soluble substance, from the carrier material.

In other embodiments, a combination of one or more layers of bioactive 260, mixtures of carrier material/bioactive, and barrier layers 262 are present on the surface of the balloon. For example, the bioactive may be mixed with a carrier material and coated onto the balloon and then over-coated with one or more barrier layer(s). In yet other embodiments, multiple layers of bioactive, or mixtures of carrier material/bioactive, possibly separated by barrier layers, are present to form a multicoated balloon. In certain embodiments, different bioactives are present in the different layers.

In certain embodiments, the carrier material and/or the barrier layer comprise a biocompatible polymer. Such polymers include both biostable and biodegradable polymers. Selection of the appropriate polymer for use in the present invention may depend upon the desired rate of release of the bioactive, the porosity of the polymer, and the rate of degradation of the polymer, for example. The coating compositions of the present invention may also include additives, such as diluents, excipients, stabilizers or the like.

In certain embodiments, the carrier material and/or the barrier layer can include a bioelastomer, PLGA, PLA, PEG, Zein, or a hydrogel. In certain other embodiments, the carrier material and/or the barrier layer includes microcrystalline cellulose, hydroxypropylmethyl cellulose, hydroxypropyl cellulose, a cellulose product, a cellulose derivative, a polysaccharide or a polysaccharide derivative. In other embodiments the carrier material and/or the barrier layer includes lactose, dextrose, mannitol, a derivative of lactose, dextrose, mannitol, starch or a starch derivative. In other embodiments, the carrier material and/or the barrier layer includes a biostable or a biodegradable material, for example, a biostable or a biodegradable polymer. Examples of such biostable and biodegradable polymers are disclosed in U.S. Publication 2004/0243225A1, published Dec. 2, 2004, which is incorporated herein by reference in its entirety.

It may be advantageous to prepare the surface of the balloon before depositing a coating thereon. Useful methods of surface preparation can include, but are not limited to cleaning; physical modifications such as etching, drilling, cutting, or abrasion; and chemical modifications such as solvent treatment, the application of primer coatings, the application of surfactants, plasma treatment, ion bombardment, covalent bonding and electrochemical methods such as electropolishing, striking, electroplating and electrochemical deposition. Such surface preparation may serve to activate the surface and promote the deposition or adhesion of the coating on the surface. Surface preparation can also selectively alter the release rate of the bioactive.

Figure 4E:
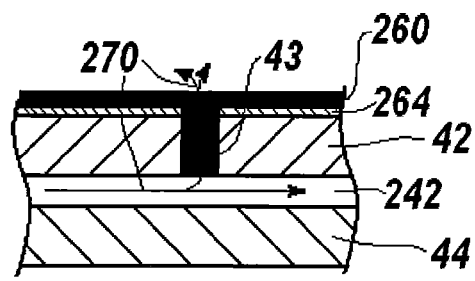

Any additional coating layers can similarly be processed to promote the deposition or adhesion of another layer, to further control the release of the bioactive 260, or to otherwise improve the biocompatibility of the surface of the layers. For example, plasma treating an additional coating layer before depositing a bioactive thereon may improve the adhesion of the bioactive, increase the amount of bioactive that can be deposited, and allow the bioactive to be deposited in a more uniform layer. According to FIG. 4E, a primer layer 264, or adhesion promotion layer, may be applied to the surface of the balloon before application of the bioactive 260. This layer may comprise, for example, silane, acrylate polymer/copolymer, acrylate carboxyl and/or hydroxyl copolymer, polyvinylpyrrolidone/vinylacetate copolymer (PVP/VA), olefin acrylic acid copolymer, ethylene acrylic acid copolymer, epoxy polymer, polyethylene glycol, polyethylene oxide, polyvinylpyridine copolymers, polyamide polymers/copolymers polyimide polymers/copolymers, ethylene vinylacetate copolymer and/or polyether sulfones. The primer layer 264 may also be similarly applied to the surfaces of the balloons in the embodiments of FIGS. 4B and 4C as appreciated by those skilled in the art. Also, it can be appreciated by those skilled in the art that various combinations of barrier layers, primer layers, bioactive layers, and the like can be configured for an elution rate that is desirable for a specific application.

In another embodiment, at least one bioactive 260 is positioned within the material of the balloon. For example, the bioactive can be mixed with a polymer and extruded to form the balloon. Such a method of manufacture is suitable for those bioactives that are stable under the conditions, particularly the temperature, required for the extrusion process. For example, in one embodiment, a powdered base silicone material is mixed with the bioactive in a solvent. The mixture is then extruded at low temperatures with the solvent evaporating as the silicone material cures. Low temperature silicone is utilized so as not to evaporate or inactivate the bioactive.

In another embodiment, at least one bioactive 260 is imbibed into the material of the balloon. U.S. Pat. No. 5,624,704, which is incorporated herein by reference in its entirety, teaches such methods of incorporating a bioactive into the material of a non-metallic device. Briefly, the device is contacted with a solvent containing the bioactive and a penetrating agent. In one embodiment, an alkalinizing agent is added to enhance the reactivity of the material of the device. The solvent is preferably an organic solvent and the penetrating agent is an ingredient that enables the bioactive to permeate the base material of the device and to become deposited within the device.

Examples of suitable organic solvents include, but are not limited to, alcohols (i.e. methanol, ethanol), ketones (acetone, methylethylketone), ethers (tetrahydrofuran), aldehydes (formaldehyde), acetonitrile, acetic acid, methylene chloride and chloroform. The penetrating agent can be any compound that can be used to promote penetration of the bioactive into the material of the device. Examples of suitable compounds are esters (i.e. ethyl acetate, propyl acetate, butyl acetate, amyl acetate, and combinations thereof), ketones (i.e. acetone and methylethylketone), methylene chloride and chloroform. The alkalinizing agent can be an organic and inorganic base including sodium hydroxide, potassium hydroxide, ammonia in water (27% ammonium hydroxide), diethylamine and triethylamine. A high ionic strength salt may act both as an alkalinizing agent and as a penetrating agent. Such salts include sodium chloride, potassium chloride and ammonium acetate.

In another embodiment, an absorbable mesh is attached to the outside surface of the balloon and at least one bioactive 260 is absorbed into this mesh. Examples of suitable mesh include mesh cotton cellulose or derivative of cellulose, cotton, cotton derivatives, alginates, dextran and rayon. Such materials may be chosen to absorb body fluids which they come into contact with and in doing so to swell and release the bioactive. Examples of bioactive application, coating configurations, and types are disclosed in U.S. Publications 2008/0300610A1, published Dec. 4, 2008, 2006/0020331A1, published Jan. 26, 2006, both which are incorporated herein by reference in their entirety.

Preferably, the bioactive 260 is an agent effective to treat or prevent restenosis (or anti-restenosis agent), such as an antisense agent, a microtubule stabilizing agent or an inhibitor of the mammalian target of rapamycin (mTOR). Preferred antisense compounds include the NeuGene Antisense compounds sold as Resten-NG and Resten-MP by AVI Biopharma, as well as rapamycin, paclitaxel and various analogs or derivatives thereof. Most preferably, the bioactives include an antisense molecule having a morpholino antisense compound with uncharged phosphorus-containing backbone linkages, and spanning the start codon of a human c-myc mRNA.

The antisense compound may have: (i) morpholino subunits linked together by phosphorodiamidate linkages, 2 atoms long, joining the morpholino nitrogen of one subunit to the 5' exocyclic carbon of an adjacent subunit; and (ii) a sequence of bases attached to the subunits and containing a therapeutically beneficial antisense nucleotide sequence. While the compound need not necessarily 100% complementary to the target sequence, it is preferably effective to stably and specifically bind to the target sequence such that expression of the target sequence is modulated. The appropriate length of the oligomer to allow stable, effective binding combined with good specificity is about 8 to 40 nucleotide base units, and preferably about 12-25 base units. Mismatches, if present, are less destabilizing toward the end regions of the hybrid duplex than in the middle. Oligomer bases that allow degenerate base pairing with target bases are also contemplated, assuming base-pair specificity with the target is maintained. The compound preferably contains internal 3-base triplet complementary to the AUG site, and bases complementary to one or more bases 5' and 3' to the start site. One preferred compound sequence is the 20 mer having the base sequence: 5'-ACG TTG AGG GGC ATC GTC GC-3', where the CAT triplet in the sequences binds to the AUG start site, the 6 bases 3' to the CAT sequence extend in the upstream (5') direction on the target, and the 11 bases 5' to the CAT sequence extend downstream on the target. This compound has enhanced solubility by virtue of having no self-annealing regions. Preferably, the bioactive is a morpholino antisense compound having (i) from 8 to 40 nucleotides, including a targeting base sequence that is complementary to a region that spans the translational start codon of a c-myc mRNA; and (ii) uncharged, phosphorous-containing intersubunit linkages, in an amount effective to reduce the risk or severity of restenosis in the patient. These bioactives are described in U.S. Pat. No. 7,094,765 and U.S. Publication 2006/0269587A1, published Nov. 30, 2006, both which are incorporated herein by reference in their entirety. While the bioactive is described with respect to certain preferred antisense compounds, any suitable bioactive in fluid form (i.e., a gas and/or a liquid) or in a fluid carrier may be delivered from the balloon catheter assembly.

In one embodiment, the bioactive 260 is an antithrombogenic agent. Devices comprising an antithrombogenic agent are particularly preferred for implantation in areas of the body that contact blood. An antithrombogenic agent is any agent that inhibits or prevents thrombus formation within a body vessel. Types of antithrombotic agents include anticoagulants, antiplatelets, and fibrinolytics. Examples of antithrombotics include but are not limited to anticoagulants such as thrombin, Factor Xa, Factor VIIa and tissue factor inhibitors; antiplatelets such as glycoprotein thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Another example of an antithrombotic agent is a nitric oxide source such as sodium nitroprussiate, nitroglycerin, S-nitroso and N-nitroso compounds. In one embodiment, a material capable of releasing nitric oxide from blood-contacting surfaces can be delivered by the device of the invention. Examples of such materials include, but are not limited to, those described in U.S. Publications 2004/0224868A1, published Nov. 11, 2004, and 2002/0115559A1, published Aug. 22, 2002, both which are incorporated herein by reference in their entirety.

Other examples of bioactives 260 suitable for inclusion in the devices of the present invention include antiproliferative/antimitotic agents including natural products such as vinca alkaloids (vinblastine, vincristine, and vinorelbine), paclitaxel, rapamycin analogs, epidipodophyllotoxins (etoposide, teniposide), antibiotics (dactinomycin (actinomycin D) daunorubicin, doxorubicin and idarubicin, anthracyclines, mitoxantrone, bleomycins, plicamycin (mithramycin) and mitomycin), enzymes (for example, L-asparaginase which systemically metabolizes L-asparagine and deprives cells which do not have the capacity to synthesize their own asparagine); antiplatelet agents such as (GP) $II_b/III_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressive (cyclosporine, tacrolimus (FK-506), sirolimus (rapamycin), tacrolimus, everolimus, azathioprine, mycophenolate mofetil); angiogenic agents: vascular endothelial growth factor (VEGF), fibroblast growth factor (FGF); angiotensin receptor blockers; nitric oxide and nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; endothelial progenitor cells (EPC); angiopeptin; pimecrolimus; angiopeptin; HMG co-enzyme reductase inhibitors (statins); metalloproteinase inhibitors (batimastat); protease inhibitors; antibodies, such as EPC cell marker targets, CD34, CD133, and AC 133/CD133; Liposomal Biphosphate Compounds (BPs), Chlodronate, Alendronate, Oxygen Free Radical scavengers such as Tempamine and PEA/NO preserver compounds, and an inhibitor of matrix metalloproteinases, MMPI, such as Batimastat. Still other bioactive agents that can be incorporated in or coated on a frame include a PPAR α (alpha)-agonist, a PPAR δ (delta)-agonist and RXR agonists, as disclosed in published U.S. Publication 2004/0073297A1 to Rohde et al., published on Apr. 15, 2004, which is incorporated herein by reference in its entirety.

In a preferred embodiment of the present invention, the bioactive is paclitaxel, rapamycin, a rapamycin derivative, an antisense oligonucleotide, or an mTOR inhibitor.

Carriers

In another aspect, besides the carrier material which may be found on the surface of the outer balloon or mixed with the bioactive in the first composition, another carrier 270 in a second composition is delivered through the fluid delivery lumen at a pressure effective to deliver the carrier through the plurality of apertures 43 in the outer balloon 42. The carrier 270, a single carrier or combined with other carrier agents, may be delivered by direct local administration to the vessel site or injury through the plurality of apertures 43 in the outer balloon 42. Type of carrier can depend on numerous factors, such as type of treatment, type of bioactive, or the like.

In some embodiments, the carrier 270 includes an imageable component, which can improve or enhance the diagnostic capabilities of imaging equipment. One of the advantages of using a carrier with an imageable component is that the carrier can be used to improve the elution rate of the bioactive while providing imageability. In one example, the carrier is a diagnostic contrast medium, such as a contrast agent. Contrast agents can be solutions, suspensions or emulsions tolerated by vessels that can be used to enhance the imageability of body vessels in radiograms, sonograms, optical imaging, magnet resonance imaging or other diagnostic imaging equipment. Contrast agents are selectively introduced to treatable regions of the body vessels during the medical procedure to determine positioning, degree and form of the stenosis, to specify the exact position of the balloon catheter, and evaluate dilatation success. By releasing the contrast agent through the apertures of the second balloon of the balloon catheter, the bioactive is transferred into the vessel wall, without additional effort or damage to the vessels. Because the contrast agent can be a carrier for the bioactive, the vessel section imaged for diagnostic purposes is also treated. Additional contrast agent at the same pressure, or at a higher or lower pressure, may be released to reach additional areas upstream and downstream from the treatable region. In one preferred embodiment, the carrier includes ISOVUE®-370 of Bracco Diagnostics (Princeton, N.J.), which includes 370 mg of organically bound iodine per mL. Various other carriers and amount and/or concentration may also be used. For example, the carrier can include other contrast agents such as iobitridol, iohexyl, iomeprol, iopamidol, iopentol, iopromide, ioverosl, ioxilan, iotrolan, iodixanol, ioxaglate, and their derivatives, or even others know in the art that are not listed. In addition, the controlled release of the bioactive can vary based on many factors including but not limited to the type of application of barrier layers described herein and the type, amount, and rate of carrier and/or carrier material described herein.

In some embodiments, carrier 270 that are biocompatible and that enhance the bioactive penetration of the target tissue can be used alone or in addition to another carrier agent, such as, e.g., saline or diagnostic contrast medium, to change the effectiveness of the carrier 270 when mixed therewith. In one example, the carrier agent can comprise a lipophilic agent to increase the lipophilicity of the bioactive, such as albumin, hydrophobic amino acids (Tryptophan, Isoleucine, Leucine, Phenylalanine, Tyrosine, Valine, Tyrosine, Methionone), ethanol, castor oil, cholesterol/fatty acids, each in a solution form, such as saline, contrast, water, or any combination thereof. The carrier may comprise dimethyl sulfoxide (DMSO) ethylenediaminetetraacetic acid (EDTA) (preferably tetrasodium). A sufficient amount of EDTA and/or DMSO would typically be diluted in water, saline, diagnostic contrast medium, or any combination mixture thereof. Bioactive forms of vitamins may also be useful as a carrier agent, such as vitamin E (tocopherols or tocotrienols), Retinol (bioactive vitamin A), cholecalciferol (bioactive vitamin D), or any derivatives thereof.

Methods of Delivery

In another embodiment, methods of delivering a bioactive to a body vessel are provided. Since the balloon catheter assembly can be provided with a therapeutically effective amount of bioactive, the clinician can avoid the steps of choosing a bioactive, measuring the bioactive, and mixing the bioactive with other components. The clinician can just simply remove the balloon catheter assembly from its packaging for introduction into the body. In operation, the balloon catheter assembly may be introduced to a body vessel by conventional medical procedures, such as the Seldinger technique, and subsequently translated through the body vessel over the wire guide to position the distal region at a point of treatment. The balloon catheter assembly may include any balloon catheter assembly disclosed herein, with preferably deflated inner and outer balloons. The inner balloon may be inflated to a desired diameter by injecting a suitable inflation fluid, such as a pressurized air, gas or liquid, through the inflation port in the manifold. For example, the inner balloon may be inflated to expand a stenosis in a body vessel such as a coronary artery. Preferably, the inner balloon is inflated until the outer balloon at least contacts a portion of a body vessel wall at a point of treatment.

A fluid can be introduced through the balloon catheter at a pressure effective to deliver it to the vessel wall through the apertures of the outer balloon. The second composition fluid containing a carrier, a diagnostic agent (e.g., x-ray contrast media), and/or a second bioactive (same as the bioactive coating or in addition to the bioactive coating) may be injected through the injection port, transported within the catheter shaft and introduced to the annular lumen between the outer balloon and the inner balloon to cause the outer balloon to move to the expanded configuration. The fluid may be pressurized in order for it to be delivered through apertures in the outer balloon before, during or after inflation of the inner balloon. While the inner balloon is inflated, introduction of the fluid is caused to pass through the apertures or weep, resulting in a therapeutically-effective amount of bioactive being delivered to the vessel wall. After expansion of the vessel and delivery of bioactive, the inner balloon is deflated and the catheter is removed from the vessel Methods for delivering the balloon catheter devices described herein to any suitable body vessel are also provided. The devices can be delivered to any suitable body vessel, including a vein, artery, biliary duct, ureteral vessel, body passage or portion of the alimentary canal. While many preferred embodiments discussed herein discuss devices having application in the treatment of stenosis or restenosis, other embodiments provide for delivery to other body vessels. In another matter of terminology there are many types of body canals, blood vessels, ducts, tubes and other body passages, and the term "vessel" is meant to include all such passages.

In some embodiments, the devices have a compressed delivery configuration with a very low profile, small collapsed diameter and great flexibility, may be able to navigate small or tortuous paths through a variety of body vessels. A low-profile device may also be useful in coronary arteries, carotid arteries, vascular aneurysms, and peripheral arteries and veins (e.g., renal, iliac, femoral, popliteal, sublavian, aorta, intercranial, etc.). Other nonvascular applications include gastrointestinal, duodenum, biliary ducts, esophagus, ureteral, reproductive tracts, trachea, and respiratory (e.g., bronchial) ducts.

In certain embodiments, the devices are used to treat a narrowing of a peripheral artery or vein. Examples of such arteries include, but are not limited to, the femoral artery, the superficial femoral artery (artery below the branch for the profunda femoris artery), the popliteal artery and the infrapopliteal artery. Examples of such veins include, but are not limited to, the femoral vein, the popliteal vein and the lesser/greater saphenous vein. Another application of the device is to open up arteriovenous fistulas that have occluded due to thrombus formation. When used to treat thrombosis, the device can also deliver an anti-coagulant. It is to be appreciated by one of ordinary skill in the art that other bioactives or the like can be introduced with the device and method described above to provide additional/redundant and/or alternative therapy to the vessel wall. For example, it may be useful to provide a paclitaxel coated balloon catheter and introduce an antisense bioactive through the apertures. In another aspect, it may be beneficial to apply the paclitaxel coated balloon generally to the entire vessel wall at the treatment site, while introducing another bioactive through the apertures to target a specific region of the vessel wall at the treatment site. The apertures can be created in a configuration to enable treatment at the specific region of the vessel wall.

EXAMPLE 1

Paclitaxel Coating of Balloon Catheter Assembly

Two 3 mm (diameter)×30 mm (length) outer balloons of the balloon catheter assemblies (Cook, Inc., Bloomington, Ind.), as described herein, are coated in the expanded state by spray coating the abluminal surface with a solution consisting of 1.5 g of paclitaxel ("PTX") per 50 mL of ethanol ("EtOH") to form a paclitaxel-ethanol solution. Following coating, the outer balloons of the coated balloon catheter assemblies are inspected and tested using UV spectrophotometry. It was determined that the spray coating applied about 1030-1110 micrograms of paclitaxel to the abluminal surface of the outer balloon of the balloon catheter assemblies.

EXAMPLE 2

Elution of Paclitaxel from Coated Balloon Catheter Assemblies

The rate of paclitaxel elution in each of the paclitaxel-coated balloon catheter assemblies described in Example 1 is analyzed in a porcine serum at 37° C. The coated balloon catheter assemblies are then divided into two groups, A and B. The coated balloon catheter assembly in Group A is designated to deliver a saline solution through the apertures of the outer balloon, while the coated balloon catheter assembly in Group B is designated to deliver a contrast media through the apertures of the outer balloon. The contrast media used is ISOVUE®-370 of Bracco Diagnostics (Princeton, N.J.), which included 370 mgl/mL of Iopamidol.

The coated balloon catheter assemblies, expanded to 4 ATM, is contacted with the porcine serum elution medium and continuously stirred for a desired period of time (e.g., at least one hour) selected to gradually dissolve the paclitaxel at a rate similar to dissolution in blood. A fluid (saline or contrast media) is then delivered through the apertures of the outer balloon into the porcine serum at a constant rate (e.g., 12 mL per hour) using a syringe pump attached to the proximal end of each coated balloon catheter assembly. A total of about 2 mL of fluid is delivered in 10 minutes. The amount of the paclitaxel dissolved is measured as a function of time by monitoring with High Performance Liquid Chromatography (HPLC) the porcine serum elution medium after contact with the coated balloon catheter assembly. A 4 mL sample of the elution medium is obtained using a pipette at certain time intervals (e.g., T=0, 1, 2, 3, 4, 5, 10, 15, 30, 45, and 60 minutes). The outer balloon of each of the coated balloon catheter assemblies is then detached from the assembly and analyzed using HPCL to measure the amount of paclitaxel left on the coated outer balloon after being in contact with the elution medium for 60 minutes.

PTX coated balloon catheters with delivery of the contrast media eluted more amount of PTX and more rapidly than PTX coated balloon catheters with delivery of the saline at certain time periods. FIG. 5 and Table 1 provide a summary of the elution rate of the paclitaxel coatings of Group A and Group B, respectively.

TABLE 1

Amount of Paclitaxel on Balloon Catheter (after 60 minutes)

| TYPE | AMOUNT |
| --- | --- |
| Group A (saline) | 742 micrograms |
| Group B | 630 micrograms |

FIG. 5 shows a graph 600 of data points depicting the amount of paclitaxel (micrograms) 602 released from the coated balloon catheter assembly at a given time period 604 of contact with the elution medium. Data line 606 reflects Group A, while data line 608 reflects Group B. For example, according to FIG. 5, after only 5 minutes of contact with the elution medium, 48.0 micrograms of PTX is released from the coated balloon catheter assembly with delivery of contrast media in comparison to 9.8 micrograms released from the coated balloon catheter assembly with delivery of saline. As shown in the data in FIG. 5, delivering contrast media through the apertures of the outer balloon of the coated balloon catheter assembly results in higher elution rates in the porcine serum elution medium. Better elution rates are seen with Group B for up to about the first 22 minutes. For example, between a time period of 2 to 10 minutes the PTX Group B balloon catheters elutes about 200% to about 500% more, as well as about 2-3 times faster, than Group A balloon catheters. Also, during the first 22 minutes, the elution rate of Group B has a range of approximately about 4.5 to about 9.6 micrograms/min, while the elution rate of Group A has a range of approximately about 1.7 to about 4.6 micrograms/min during the same time, according to FIG. 5.

Table 1 shows the amount of paclitaxel left on the outer balloon after contact with the elution medium for a period of 60 minutes. An amount of about 630 micrograms of PTX is measured on the coated balloon catheter assembly with delivery of contrast media in comparison to about 742 micrograms of paclitaxel from the coated balloon catheter assembly with delivery of saline. As shown in the data in Table 1, Group B balloon catheters results in a lower amount of PTX (about 15% or less) on the outer balloon than Group A balloon catheters. In other words, not only did the paclitaxel coated balloon catheter delivering a contrast media elute more paclitaxel and elute more quickly, but also less paclitaxel was left on the outer balloon after 60 minutes than the coated balloon catheter delivering saline.

A therapeutically effective amount of bioactive desired for release to a target site can vary depending on several factors. Data line 608 in FIG. 5 indicates the elution rate and the amount of released bioactive for a weeping fluid having 100% contrast media in a given coated balloon catheter assembly with a pre-determined weight of bioactive. Data line 606 in FIG. 5 indicates the same for a weeping fluid having 100% saline. By varying the mixture of saline and contrast agent in the weeping fluid, the elution rate and amount of released bioactive can be changed and thus suitably controlled for a desired amount of bioactive release. For example, for a procedure with a desired time of five minutes, the amount of released bioactive for a weeping fluid having 100% contrast media is about 50 micrograms, and for 100% saline is about 10 micrograms. When the desired amount of released bioactive is 30 micrograms for a five minute procedure, a 50/50 mixture of saline and contrast agent can be used. As appreciated by persons skilled in the art, when more bioactive release is desired the relative amount of contrast agent can be increased accordingly, e.g., 25/75, and vice versa when less is needed, e.g., 75/25. Changing the mixture ratio of two or more carrier agents in the weeping fluid can provide the clinician the capability to control and/or vary the release of bioactive to a therapeutically effective amount for a coated balloon catheter assembly with a pre-determined weight of bioactive.

Those of skill in the art will appreciate that other embodiments and variants of the structures and methods described above may be practiced within the scope of the present invention. It is therefore intended that the foregoing detailed description be regarded as illustrative rather than limiting, and that it be understood that it is the following claims, including all equivalents, that are intended to define the spirit and scope of this invention.

The invention claimed is:

1. A method of delivering a bioactive to a point of treatment within a body vessel, the method comprising the steps of:
positioning a balloon catheter at said point of treatment within said body vessel, the balloon catheter including a catheter shaft having an inflation lumen and a fluid delivery lumen, a deflated inner balloon mounted on the catheter shaft and in communication with the inflation lumen, a compressed outer balloon mounted around at least a portion of the inner balloon, the outer balloon including a plurality of apertures and the inner balloon not including any apertures, the inner balloon and the outer balloon being configured and oriented such that an annular lumen is defined between the inner and outer balloons when the inner balloon is in an inflated configuration and the outer balloon is in an expanded configuration, the annular lumen being in communication with the fluid delivery lumen and the plurality of apertures; and a first composition comprising a bioactive disposed on a portion of a surface of at least one of the outer balloon and the inner balloon;

inflating the inner balloon to the inflated configuration to place the outer balloon in contact with a wall of said body vessel;

introducing a second composition comprising a carrier that enhances the elution rate of the bioactive compared to saline for a time period of 2 to 10 minutes, wherein the carrier is a diagnostic x-ray contrast medium, the second composition being introduced through the fluid delivery lumen and the annular lumen to move the outer balloon to the expanded configuration at a pressure effective to deliver the second composition to said body vessel wall through the apertures of the outer balloon; and maintaining contact of the outer balloon with said body vessel wall for a time sufficient to deliver a therapeutically effective amount of bioactive to said treatment site within said body vessel wall.

2. The method of claim 1, where the bioactive is selected from a group consisting of an anti-restenosis agent, an antisense agent, an antithrombogenic agent, an antiproliferative agent, and antimitotic agent.

3. The method of claim 1, where the carrier is selected from a group consisting of iobitridol, iohexyl, iomeprol, iopamidol, iopentol, iopromide, ioverosl, ioxilan, iotrolan, iodixanol, ioxaglate, and their derivatives.

4. The method of claim 1, wherein the bioactive comprises paclitaxel, and the carrier includes iopamidol.

5. The method of claim 1, further comprising controlling the therapeutically effective amount of bioactive delivered by mixing a first carrier with a second carrier in order to form the second composition.

6. The method of claim 1, further comprising a barrier layer disposed on the first composition.

7. The method of claim 1, further comprising a primer layer disposed between the first composition and the surface of the balloon.

8. The method of claim 1, where the bioactive is selected from a group consisting of paclitaxel, rapamycin, a rapamycin derivative, an antisense oligonucleotide, and mTOR inhibitor.

9. The method of claim 1, where the catheter shaft includes an outer sleeve disposed along a portion of the catheter shaft, and a first tubular member to define the inflation lumen and a second tubular member to define the fluid delivery lumen disposed within the outer sleeve, the catheter shaft further comprising a thermoformable polymer disposed within the outer sleeve and about the first and second tubular members, where each of the first and second tubular members comprises fluorinated hydrocarbon tubular liner, and the thermoformable polymer has a lower melting temperature than the fluorinated hydrocarbon tubular liner.

10. The method of claim 9, further comprising a stiffening member disposed within a portion of the catheter shaft, where a portion of the stiffening member is surrounded by a thermoformable polymer, where the stiffening member is in non-translatable contact with the thermoformable polymer.

11. The method of claim 1, where the first composition is disposed on a portion of the exterior surface of the outer balloon.

12. The method of claim 1, where the first composition is disposed on a portion of the interior surface of the outer balloon.

13. The method of claim 1, where the first composition is disposed on a portion of the exterior surface of the inner balloon.

14. The method of claim 1, where the first composition includes a solvent.

15. The method of claim 14, where the second composition further comprises a mixture of saline and the diagnostic x-ray contrast media.

16. The method of claim 1, where the bioactive comprises an antisense agent.

17. The method of claim 1, where the second composition further comprises a mixture of saline and the diagnostic x-ray contrast media.

18. The method of claim 1, where the bioactive comprises paclitaxel.

19. The method of claim 1, where the carrier is selected from a group consisting of iobitridol, iohexyl, iomeprol, iopamidol, iopentol, iopromide, ioverosl, ioxilan, iotrolan, iodixanol, ioxaglate, and their derivatives, the second composition further comprises a mixture of saline and the diagnostic x-ray contrast media, the bioactive is selected from a group consisting of paclitaxel, rapamycin, a rapamycin derivative, an antisense oligonucleotide, and mTOR inhibitor, and the first composition is disposed on a portion of the interior surface of the outer balloon or on a portion of the exterior surface of the inner balloon.

20. The method of claim 1, where the bioactive is selected from a group consisting of an anti-restenosis agent, an antisense agent, an antithrombogenic agent, an antiproliferative agent, and antimitotic agent, further comprising controlling the therapeutically effective amount of bioactive delivered by mixing a first carrier with a second carrier in order to form the second composition, a barrier layer disposed on the first composition, and a primer layer disposed between the first composition and the surface of the balloon.

* * * * *